(12) United States Patent
Matov et al.

(10) Patent No.: US 11,478,334 B2
(45) Date of Patent: Oct. 25, 2022

(54) SYSTEMS AND METHODS FOR NONLINEAR TOOTH MODELING

(71) Applicant: Align Technology, Inc., San Jose, CA (US)

(72) Inventors: Vadim Matov, San Jose, CA (US);
Sergei Brodsky, San Jose, CA (US);
Bastien Pesenti, San Jose, CA (US);
Yuri Syrov, San Jose, CA (US); Ping Tang, Milpitas, CA (US); Manlio Fabio Valdivieso Casique, Santa Clara, CA (US); Olga Matusevich, Moscow (RU); Igor Kvasov, Los Altos, CA (US)

(73) Assignee: Align Technology, Inc., San Jose, CA (US)

( * ) Notice: Subject to any disclaimer, the term of this patent is extended or adjusted under 35 U.S.C. 154(b) by 83 days.

(21) Appl. No.: 16/730,865

(22) Filed: Dec. 30, 2019

(65) Prior Publication Data
US 2020/0214800 A1    Jul. 9, 2020

Related U.S. Application Data

(60) Provisional application No. 62/788,025, filed on Jan. 3, 2019.

(51) Int. Cl.
*A61C 7/00* (2006.01)
*A61C 7/08* (2006.01)
(Continued)

(52) U.S. Cl.
CPC ............... *A61C 7/002* (2013.01); *A61C 7/08* (2013.01); *G06T 17/20* (2013.01); *G16H 20/00* (2018.01); *G06T 2207/30036* (2013.01)

(58) Field of Classification Search
CPC .......... A61C 7/002; A61C 7/08; G16H 20/00; G16H 50/50; G06T 17/20;
(Continued)

(56) References Cited

U.S. PATENT DOCUMENTS 2,467,432 A   4/1949 Kesling
3,407,500 A   10/1968 Kesling
(Continued)

FOREIGN PATENT DOCUMENTS

AU    3031677 A    5/1979
AU    517102 B2    7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Emily C Terrell
*Assistant Examiner* — Molly Wilburn
(74) *Attorney, Agent, or Firm* — Wilson Sonsini Goodrich & Rosati

(57) ABSTRACT

Systems and methods of generating an orthodontic model are disclosed. The method may include: generating an initial model of a patient dentition; generating a target model of the patient dentition; defining a plurality of caps and a plurality of links, wherein each link connects two of the plurality of caps; generating a relaxed model of a dental appliance from the plurality of caps and the plurality of links; generating a deformed model of a dental appliance from the plurality of caps and plurality of links; and determining a plurality of movements, wherein the plurality of moments transform the relaxed model to the deformed model and wherein the moments are configured to direct the patient dentition from the initial model to the target model.

22 Claims, 14 Drawing Sheets

(51) Int. Cl.
*G16H 20/00* (2018.01)
*G06T 17/20* (2006.01)

(58) Field of Classification Search
CPC ... G06T 2207/30036; G06T 2219/2021; G06T 2210/41; G06T 19/02
See application file for complete search history.

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van Der Zel et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump et al. |
| 5,880,962 A | 3/1999 | Andersson et al. |
| 5,934,288 A | 8/1999 | Avila et al. |
| 5,957,686 A | 9/1999 | Anthony et al. |
| 5,964,587 A | 10/1999 | Sato et al. |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda et al. |
| 6,049,743 A | 4/2000 | Baba et al. |
| 6,062,861 A | 5/2000 | Andersson |
| 6,068,482 A | 5/2000 | Snow et al. |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren et al. |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier et al. |
| 6,398,548 B1 | 6/2002 | Muhammad et al. |
| 6,402,707 B1 | 6/2002 | Ernst et al. |
| 6,450,807 B1 | 9/2002 | Chishti et al. |
| 6,482,298 B1 | 11/2002 | Bhatnagar et al. |
| 6,524,101 B1 | 2/2003 | Phan et al. |

(56) References Cited

U.S. PATENT DOCUMENTS

| | | | |
|---|---|---|---|
| 6,554,611 | B2 | 4/2003 | Shishti et al. |
| 6,572,372 | B1 | 6/2003 | Phan et al. |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 6,749,414 | B1 | 6/2004 | Hanson et al. |
| 6,830,450 | B2 | 12/2004 | Knopp et al. |
| 7,892,474 | B2 | 2/2011 | Shkolnik et al. |
| 9,205,601 | B2 | 12/2015 | Desimone et al. |
| 9,211,678 | B2 | 12/2015 | Desimone et al. |
| 9,216,546 | B2 | 12/2015 | Desimone et al. |
| 9,321,215 | B2 | 4/2016 | Dudley |
| 9,511,543 | B2 | 12/2016 | Tyler |
| 10,881,486 | B2 * | 1/2021 | Wen .................... A61C 7/08 |
| 10,980,613 | B2 * | 4/2021 | Shanjani ............... G06F 3/011 |
| 11,013,581 | B2 * | 5/2021 | Sabina .................. A61B 1/24 |
| 2002/0006597 | A1 | 1/2002 | Andreiko et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer et al. |
| 2004/0128010 | A1 | 7/2004 | Pavlovskaia et al. |
| 2005/0055118 | A1 | 3/2005 | Nikolskiy et al. |
| 2016/0095668 | A1 * | 4/2016 | Kuo .................... A61C 7/00 703/6 |
| 2018/0189434 | A1 * | 7/2018 | Zhou .................... G16H 50/50 |
| 2019/0321135 | A1 * | 10/2019 | Wen .................... A61C 7/08 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et al., "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler, "3D Mapping of Maxillo-Facial Prosthesis," AADR Abstract #607, 2 pages total, (1980).
Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin, in Orthod., 7(4):223-232 (Dec. 2001).
Begole et al., "A Computer System for the Analysis of Dental Casts," The Angle Orthod., 51(3):253-259 (Jul. 1981).
Bernard et al.," Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253(1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL< http://astronomy.swin.edu.au/—pbourke/prolection/coords>.
Boyd et al., "Three Dimensional Diagnosis and Orthodontic Treatment of Complex Malocclusions With the Invisalign Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form in Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.

(56) References Cited

OTHER PUBLICATIONS

Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992.
Definition for gingiva. Dictionary.com p. 1-3. Retrieved from the internet Nov. 5, 2004< http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
DENT-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al., "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet:< http://wscg.zcu.cz/wscg98/papers98/Strasser 98.pdf, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gttleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxillofacial Surgery," AAOMS, 3 pages total, (Sep. 13, 1990).
Guess et al., "Computer Treatment Estimates in Orthodontics and Orthognathic Surgery," JCO, pp. 262-328 (Apr. 1989).
Heaven et al., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulating stressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informationen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System. Allesee Orthodontic Appliances—Pro Lab. 1 page (1998).
JCO Interviews, "Craig Andreiko , DDS, MS on the Elan and Orthos Systems," JCO, pp. 459-468 (Aug. 1994).
JCO Interviews, "Dr. Homer W. Phillips on Computers in Orthodontic Practice, Part 2," JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11): 1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945;31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.

(56) References Cited

OTHER PUBLICATIONS

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
Mccann, "Inside the ADA," J. Amer. Dent. Assoc., 118:286-294 (Mar. 1989).
Mcnamara et al., "Invisible Retainers," J. Clin. Orthod., pp. 570-578 (Aug. 1985).
Mcnamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAMInlays: Aesthetics and Durability in a Single Appointment," Dent. Today, 9(8):20, Oct. 23-23, 1990.
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sept. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www. essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolaryngol Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in derZahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No. Braces Treatment, Allesee Orthodontic Appliances—Pro Lab product information, 6 pages (2003).
The Choice Is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml, 5 pages (May 19, 2003).
The Choice is Clear: Red, White & Blue . . . The Simple, Affordable, No-Braces Treatment, Allesee HJ Orthodontic Appliances—Pro Lab product information for patients, (http://ormco.com/aoa/appliancesservices/RWB/patients.html), 2 pages (May 19, 2003).
The Red, White & Blue Way to Improve Your Smile!, Allesee Orthodontic Appliances—Pro Lab product information for patients, 2 pages (1992).
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).

(56) References Cited

OTHER PUBLICATIONS

Van Der Zel, "Ceramic-Fused-to-Metal Restorations with a New CAD/CAM System," Quintessence Int., 24(11)769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 388-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970)58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Interneton Nov. 5, 2004, URL(http://wscg.zcu.cz/wscg98/wscg98.h).
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf, of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances—Pro Lab product information for patients, 2 pages (2002).

* cited by examiner

SYSTEMS AND METHODS FOR NONLINEAR TOOTH MODELING

CROSS-REFERENCE

This application claims the benefit of U.S. Provisional Application No. 62/788,025, filed Jan. 3, 2019, which application is incorporated herein by reference.

TECHNICAL FIELD

The technical field generally relates to system and methods of correcting malocclusions of teeth. More particularly, the technical field relates to system and methods of accurately and realistically generating models of tooth force systems, and systems and methods of determining clinically effective orthodontic aligners for teeth.

BACKGROUND

Existing methods for orthodontic modeling of forces and moments may be time consuming, computationally expensive, and/or inaccurate. Methods of modeling forces and modeling based on finite element analysis may suffer from non-convergence and/or excessive time consumption.

SUMMARY

The present disclosure addresses technical needs for fast and accurate models of force and/or moment systems to predict the effects of treatment plans and design/manufacture effective dental appliances. When designing and/or manufacturing dental appliances, such as aligners, it may be useful to optimize the position(s) and/or orientation(s) of portions of the dental appliances. Doing so may ensure comfort (e.g., dental appliances are fitting as intended) and more accurate implementation of various functionalities (e.g., that force systems and/or torques applied as part of a treatment plan are being applied as intended). The implementations described herein may accurately calculate force systems (forces, torques, etc.) of dental appliances by modeling the regions that surround a specific tooth/teeth as "caps" and modeling various translational and/or rotational relationships between caps. In some implementations, relaxed and/or deformed models of a dental appliance are identified and used to map force(s)/torque(s) between caps and/or links. Techniques described herein may be useful to design/manufacture dental appliances that call for application of complex and/or non-linear force(s)/torque(s) on a patient's dentition.

A computer-implemented method of generating an orthodontic model of tooth movements is disclosed. The computer-implemented method my comprise generating an initial model of a patient dentition, the initial three-dimensional model comprising a first, three-dimensional representation of the patient dentition at a stage of a treatment plan, generating a target model of the patient dentition, the target three-dimensional model comprising a second, three-dimensional representation of the patient dentition after the stage of the treatment plan, defining a plurality of caps and a plurality of links, wherein each cap of the plurality of caps represents a set of contact points on a tooth of the dentition, and wherein each link of the plurality of links represents a connection between two of the plurality of caps, generating a relaxed model of a dental appliance from the plurality of caps and the plurality of links, the relaxed model of the dental appliance representing physical properties of the dental appliance at a first state, generating a deformed model of a dental appliance from the plurality of caps and plurality of links, the deformed model of the dental appliance representing the physical properties of the dental appliance at a second state corresponding to a use of the dental appliance, determining a plurality of transformational parameters, wherein the plurality of transformational parameters transform the relaxed model to the deformed model and wherein the plurality of transformational parameters are configured to direct the patient dentition from the initial model to the target model, and using the plurality of transformation parameters to design the dental appliance.

In some embodiments, the plurality of transformation parameters comprise one or more of a plurality of forces and a plurality of moments.

In some embodiments, the computer implemented method may include mapping the relaxed model onto the deformed model or expressing the relaxed model and the deformed model in an elastic coordinate system.

In some embodiments, the computer implemented method may include determining a force system for each pair of teeth. The method may also include summing the force system for each pair to determine a total force for a whole arch system.

In some embodiments, the computer implemented method may include determining a moment system for each pair of teeth. The method may also include summing the moment system for each pair to determine a total moment for a whole arch system.

In some embodiments, a whole arch system has no total force or total moment.

In some embodiments, the initial model of patient dentition comprises a scan of the patient dentition or a mold of the patient dentition. Each of the plurality of caps may include a reduced dimensional surface which represents the patient dentition. Each of the plurality of links may include a Hookian stiffness parameter.

In some embodiments, the method may include repeating the determining a plurality of moments for a second stage in the treatment plan.

In some embodiments, the method may include fabricating one or a plurality of dental appliances.

In some embodiments, the method reduces a time to generate a force model by 10% relative solid model analysis.

In some embodiments, the method includes creating or developing the treatment plan based on the plurality of moments or determining an effectiveness of the treatment plan based on the plurality of moments.

In some embodiments, the method includes creating a plurality of treatment plans based on the plurality of moments and selecting a target treatment plan from the plurality of treatment plans. In some embodiments, the selecting a target treatment plan is based on a time efficiency of the target treatment plan. In some embodiments, the selecting a target treatment plan is based on a therapeutic effectiveness of the target treatment plan.

In some embodiments, the determining a plurality of tooth moments is performed "chair side".

A computer-implemented method of generating an orthodontic treatment plan is also disclosed. The method may include generating an initial model of a patient dentition, the initial three-dimensional model comprising a first, three-dimensional representation of the patient dentition at a stage of a treatment plan, generating a target model of the patient dentition, the target three-dimensional model comprising a second, three-dimensional representation of the patient dentition after the stage of the treatment plan, defining a plurality of caps and a plurality of links, wherein each cap of the plurality of caps represents a set of contact points on a tooth of the dentition, and wherein each link of the plurality of links represents a connection between two of the plurality of caps, generating a relaxed model of a dental appliance from the plurality of caps and the plurality of links, the relaxed model of the dental appliance representing physical properties of the dental appliance at a first state, generating a deformed model of a dental appliance from the plurality of caps and plurality of links, the deformed model of the dental appliance representing the physical properties of the dental appliance at a second state corresponding to a use of the dental appliance, determining a plurality of transformational parameters, wherein the plurality of transformational parameters transform the relaxed model to the deformed model and wherein the plurality of transformational parameters are configured to direct the patient dentition from the initial model to the target model, using the plurality of transformation parameters to design the dental appliance, and providing the dental appliance to a patient.

A system for generating an orthodontic treatment plan is disclosed. The system may include memory storing computer-program instructions one or more physical processors coupled to the memory, the one or more physical processors configured to implement a computer-implemented method using the computer-program instructions, the computer-implemented method generating a virtual depiction of an orthodontic treatment of a patient, the computer-implemented method comprising: generating an initial model of a patient dentition, the initial three-dimensional model comprising a first, three-dimensional representation of the patient dentition at a stage of a treatment plan, generating a target model of the patient dentition, the target three-dimensional model comprising a second, three-dimensional representation of the patient dentition after the stage of the treatment plan, defining a plurality of caps and a plurality of links, wherein each cap of the plurality of caps represents a set of contact points on a tooth of the dentition, and wherein each link of the plurality of links represents a connection between two of the plurality of caps, generating a relaxed model of a dental appliance from the plurality of caps and the plurality of links, the relaxed model of the dental appliance representing physical properties of the dental appliance at a first state, generating a deformed model of a dental appliance from the plurality of caps and plurality of links, the deformed model of the dental appliance representing the physical properties of the dental appliance at a second state corresponding to a use of the dental appliance, determining a plurality of transformational parameters, wherein the plurality of transformational parameters transform the relaxed model to the deformed model and wherein the plurality of transformational parameters are configured to direct the patient dentition from the initial model to the target model, and using the plurality of transformation parameters to design the dental appliance.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
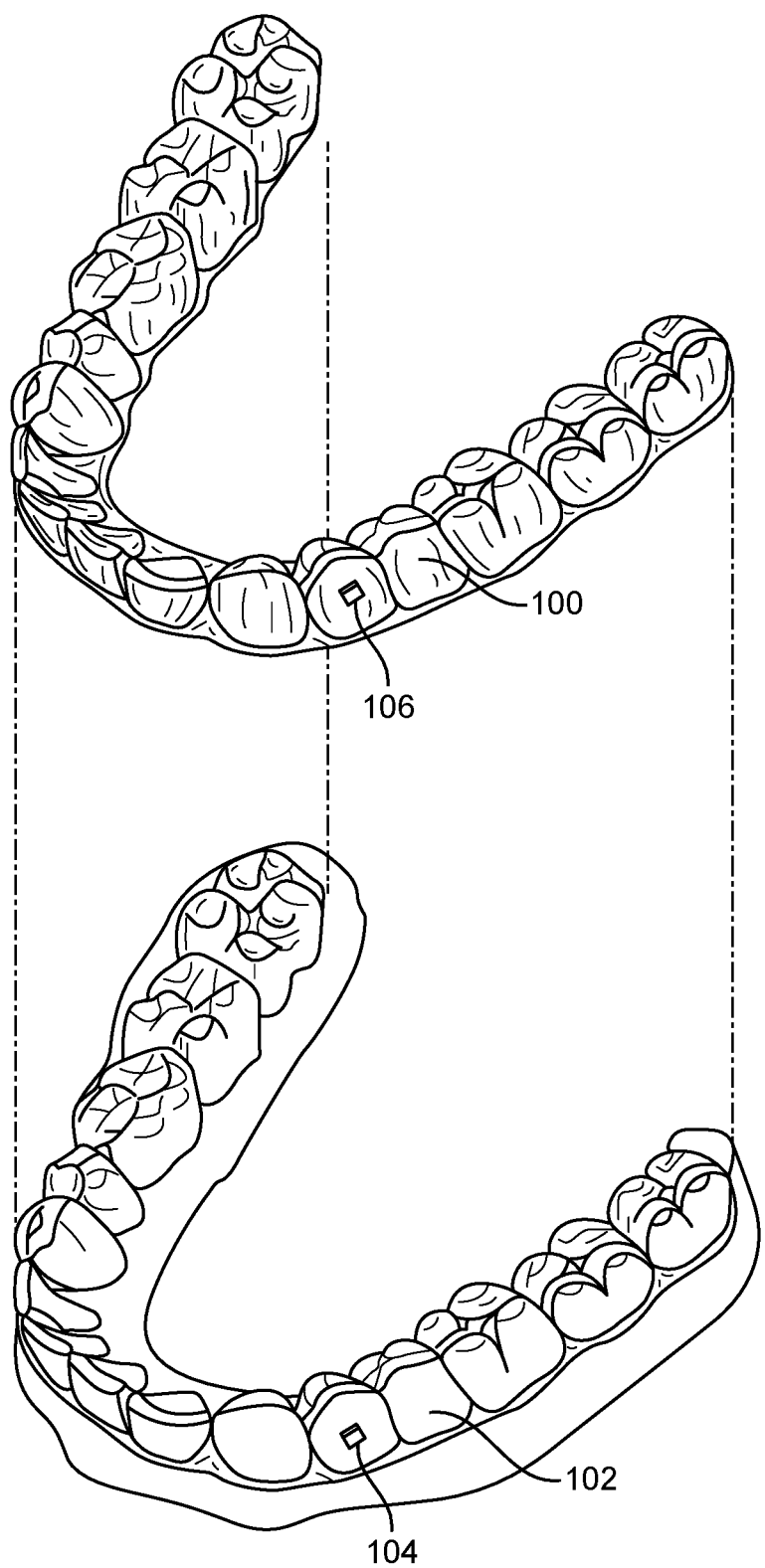
FIG. 1A illustrates a tooth repositioning appliance, in accordance with one or more embodiments herein.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the invention as described herein.

As used herein the terms "dental appliance," and "tooth receiving appliance" are treated synonymously. As used herein, a "dental positioning appliance" or an "orthodontic appliance" may be treated synonymously, and may include any dental appliance configured to change the position of a patient's teeth in accordance with a plan, such as an orthodontic treatment plan. A "dental positioning appliance" or "orthodontic appliance," as used herein, may include a set of dental appliances configured to incrementally change the position of a patient's teeth over time. As noted herein, dental positioning appliances and/or orthodontic appliances may comprise polymeric appliances configured to move a patient's teeth in accordance with an orthodontic treatment plan.

As used herein the term "and/or" may be used as a functional word to indicate that two words or expressions are to be taken together or individually. For example, the phrase "A and/or B" encompasses A alone, B alone, and A and B together. Depending on context, the term "or" need not exclude one of a plurality of words/expressions. As an example, the phrase "A or B" need not exclude A and B together.

As used herein the terms "torque" and "moment" are treated synonymously.

As used herein a "moment" may encompass a force acting on an object such as a tooth at a distance from a center of resistance. The moment may be calculated with a vector cross product of a vector force applied to a location corresponding to a displacement vector from the center of resistance, for example. The moment may comprise a vector pointing in a direction. A moment opposing another moment may encompass one of the moment vectors oriented toward a first side of the object such as the tooth and the other moment vector oriented toward an opposite side of the object such as tooth, for example. Any discussion herein referring to application of forces on a patient's teeth is equally applicable to application of moments on the teeth, and vice-versa.

As used herein a "plurality of teeth" may encompass two or more teeth. A plurality of teeth may, but need not, comprise adjacent teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The embodiments disclosed herein may be well suited for moving one or more teeth of the first group of one or more teeth or moving one or more of the second group of one or more teeth, and combinations thereof.

Systems and Methods for Determining Tooth Transformational Parameters Based on a Nonlinear Model Systems and methods of the present disclosure provide an orthodontic model of tooth moments. In some examples the method may comprise generating an initial model of a patient dentition, the initial three-dimensional model comprising a first, three-dimensional representation of the patient dentition at a stage of a treatment plan. In some examples, the methods herein may comprise generating a target model of the patient dentition, the target three-dimensional model comprising a second, three-dimensional representation of the patient dentition after the stage of the treatment plan.

In some examples the method may comprise defining a plurality of caps and a plurality of links to model application of a force system to be applied according to the treatment plan. A "cap," as used herein, may refer to a representation of a first portion of a dental appliance that interacts with a tooth or teeth. An example of such first a portion is a part of a polymeric aligner that contacts a tooth or teeth. For instance, a cap may represent contact points of a dental appliance against a tooth. A cap may further represent location(s) of these first portions, size(s) of these first portions, etc. In various implementations, a cap may be associated with a first rigidity.

A "link," as used herein, may refer to a second portion of a dental appliance that connects two or more caps. As noted herein, a links may connect two of the plurality of caps. An example of such a second portion is an interproximal region of a polymeric aligner. A link may represent the area between contact points of a dental appliance against two teeth. A link may further represent location(s) of these second portions, size(s) of these second portions, etc. In various implementations, a link may be associated with a second rigidity that is different from the first rigidity. The second rigidity may have a value corresponding to a greater rigidity than the first rigidity. (This may accommodate the fact that interproximal regions of an aligner may be more rigid than the portions of the aligner that interact with specific teeth.)

In some examples methods herein may comprise identifying a relaxed model of a dental appliance using the plurality of caps and the plurality of links. A "relaxed model of a dental appliance," as used herein, may refer to a model of a dental appliance that represents physical properties of the dental appliance when it is manufactured (e.g., through the indirect or direct fabrication techniques described herein). In some examples, the methods herein may comprise identifying a deformed model of the dental appliance to model an approximate use of the dental appliance. A "deformed model of a dental appliance," as used herein, may refer to a model of a dental appliance that represents physical properties of the dental appliance after it has been used in its environment. For instance, a deformed model of an aligner may represent the physical properties of an aligner after the aligner has been inserted into a patient's mouth. A deformed model of an aligner may represent the physical properties of an aligner after the aligner has resided in a patient's mouth for a specified amount of time (e.g., a number of hours, days, etc.). A deformed model of an aligner may represent physical properties of an aligner after its physical properties when manufactured have changed beyond a specified threshold (e.g., after its physical properties when manufactured have sufficiently relaxed due to use in an intraoral or humid environment).

In some examples, the methods herein may comprise identifying relationships (e.g., differences) between the relaxed model of a dental appliance and a deformed model of the dental appliance. The relationships may form the basis of a map between the relaxed model of the dental appliance and a deformed model of the dental appliance. The map may include one or more common attributes, such as common reference points (e.g., common center points) and/or common axes. The map may form the basis of an elastic coordinate system for the dental appliance.

In some examples, methods herein may comprise using the caps and/or links of the relaxed model of the dental appliance and/or the deformed model of the dental appliance to model applying the dental appliance to the initial model of the patient dentition. In some implementations, deviations between the deformed model of the dental appliance and the initial model of the patient dentition may be used to identify application of force(s), torque(s), etc. to move the patient dentition from an initial position (e.g., corresponding to the initial model) toward a target position (e.g., corresponding to the target position). As noted herein, force(s), torque(s), etc. may be calculated by analyzing caps, identifying properties of links, and/or obtaining force(s)/torque(s), etc. using relevant sums of pairs of forces on those caps.

The embodiments disclosed herein may be well suited for combination with one or more commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides orthodontic appliances and related systems, methods, and devices. Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration. Repositioning of teeth may be accomplished through other series of removable orthodontic and/or dental appliances, including polymeric shell appliances.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining. Additionally, though reference is made herein to orthodontic appliances, at least some of the techniques described herein may apply to restorative and/or other dental appliances, including without limitation crowns, veneers, teeth-whitening appliances, teeth-protective appliances, etc.

Appliances

FIG. 1A illustrates an exemplary tooth repositioning appliance or aligner 100 that can be worn by a patient in order to achieve an incremental repositioning of individual teeth 102 in the jaw. The appliance can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. The physical model (e.g., physical mold) of teeth can be formed through a variety of techniques, including 3D printing. The appliance can be formed by thermoforming the appliance over the physical model. In some embodiments, a physical appliance is directly fabricated, e.g., using additive manufacturing techniques, from a digital model of an appliance. In some embodiments, the physical appliance may be created through a variety of direct formation techniques, such as 3D printing. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some or most, and even all, of the teeth will be repositioned at some point during treatment. Teeth that are moved can also serve as a base or anchor for holding the appliance as it is worn by the patient.

In some embodiments, no wires or other means will be provided for holding an appliance in place over the teeth. In some cases, however, it may be desirable or necessary to provide individual attachments or other anchoring elements 104 on teeth 102 with corresponding receptacles or apertures 106 in the appliance 100 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Optionally, in cases involving more complex movements or treatment plans, it may be beneficial to utilize auxiliary components (e.g., features, accessories, structures, devices, components, and the like) in conjunction with an orthodontic appliance. Examples of such accessories include but are not limited to elastics, wires, springs, bars, arch expanders, palatal expanders, twin blocks, occlusal blocks, bite ramps, mandibular advancement splints, bite plates, pontics, hooks, brackets, headgear tubes, springs, bumper tubes, palatal bars, frameworks, pin-and-tube apparatuses, buccal shields, buccinator bows, wire shields, lingual flanges and pads, lip pads or bumpers, protrusions, divots, and the like. In some embodiments, the appliances, systems and methods described herein include improved orthodontic appliances with integrally formed features that are shaped to couple to such auxiliary components, or that replace such auxiliary components.

Figure 1B:
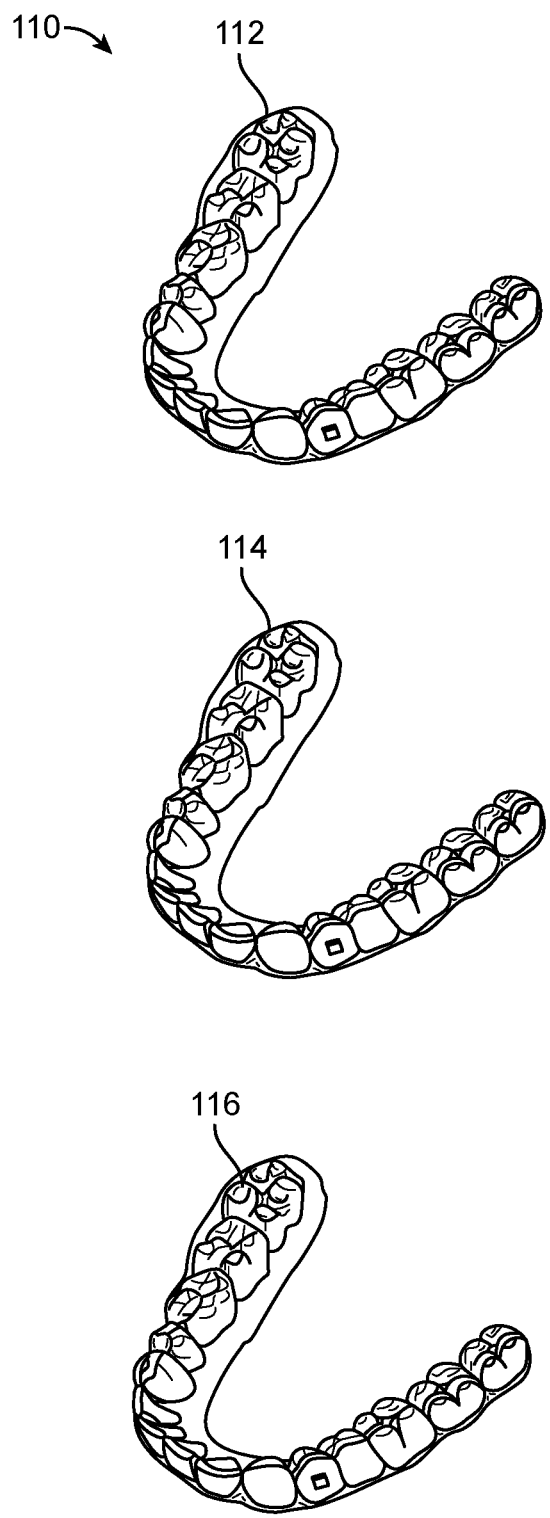
FIG. 1B illustrates a tooth repositioning system, in accordance with one or more embodiments herein.

FIG. 1B illustrates a tooth repositioning system 110 including a plurality of appliances 112, 114, 116. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement towards a target tooth arrangement by placing a series of incremental position adjustment appliances over the patient's teeth. For example, the tooth repositioning system 110 can include a first appliance 112 corresponding to an initial tooth arrangement, one or more intermediate appliances 114 corresponding to one or more intermediate arrangements, and a final appliance 116 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 1C:
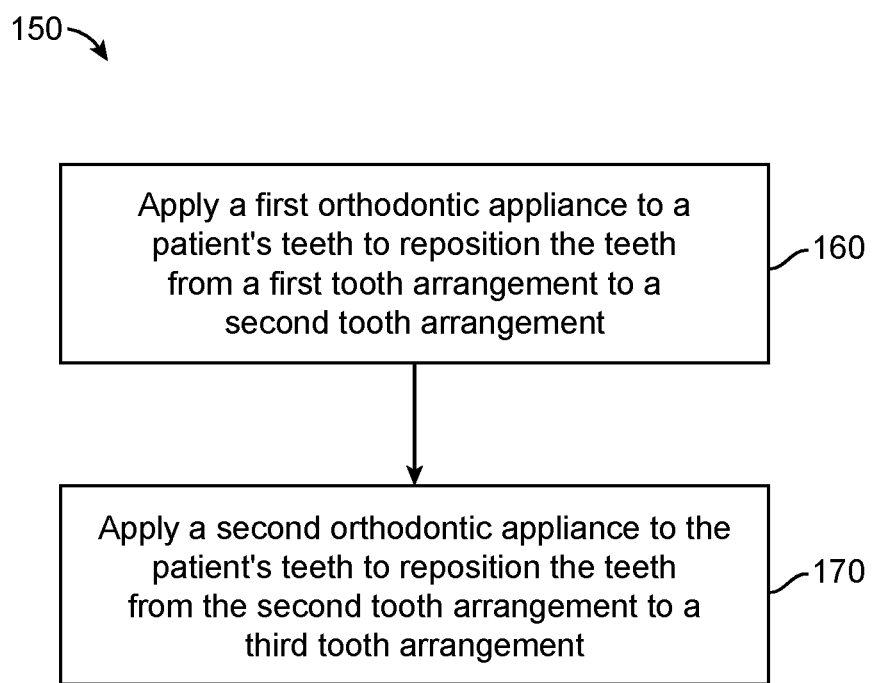
FIG. 1C illustrates a method of orthodontic treatment using a plurality of appliances, in accordance with one or more embodiments herein.

FIG. 1C illustrates a method 150 of orthodontic treatment using a plurality of appliances, in accordance with embodiments. The method 150 can be practiced using any of the appliances or appliance sets described herein. In block 160, a first orthodontic appliance is applied to a patient's teeth in order to reposition the teeth from a first tooth arrangement to a second tooth arrangement. In block 170, a second orthodontic appliance is applied to the patient's teeth in order to reposition the teeth from the second tooth arrangement to a third tooth arrangement. The method 150 can be repeated as necessary using any suitable number and combination of sequential appliances in order to incrementally reposition the patient's teeth from an initial arrangement to a target arrangement. The appliances can be generated all at the same stage or in sets or batches (at the beginning of a stage of the treatment, at an intermediate stage of treatment, etc.), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Appliance Fabrication

The various embodiments of the orthodontic appliances presented herein can be fabricated in a wide variety of ways. In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances herein can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances herein can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances herein. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object's geometry can be used, referred to herein as "continuous direct fabrication." Various types of continuous direct fabrication methods can be used. As an example, in some embodiments, the appliances herein are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, (corresponding to U.S. Pat. Nos. corresponding to U.S. Pat. Nos. 9,205,601, 9,216,546, and 9,211,678) the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous 3D path in order to form the object. Such methods are described in U.S. Patent Publication No. 2014/0061974, corresponding to U.S. Pat. No. 9,511,543, the disclosures of which are incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, corresponding to U.S. Pat. No. 9,321,215, the disclosures of which are incorporated herein by reference in its entirety.

The direct fabrication approaches provided herein are compatible with a wide variety of materials, including but not limited to one or more of the following: polymer matrix reinforced with ceramic or metallic polymers, a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step using the same fabrication machine and method. For instance, a multi-tip extrusion apparatus can be used to selectively dispense multiple types of materials (e.g., resins, liquids, solids, or combinations thereof) from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed. The relative arrangement of the first and second portions can be varied as desired, e.g., the first portion can be partially or wholly encapsulated by the second portion of the object. The sequential manufacturing steps can be performed using the same fabrication machine or different fabrication machines, and can be performed using the same fabrication method or different fabrication methods. For example, a sequential multi-manufacturing procedure can involve forming a first portion of the object using stereolithography and a second portion of the object using fused deposition modeling.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the 3D geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every $n^{th}$ build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

Although various embodiments herein are described with respect to direct fabrication techniques, it shall be appreciated that other techniques can also be used, such as indirect fabrication techniques. In some embodiments, the appliances herein (or portions thereof) can be produced using indirect fabrication techniques, such as by thermoforming over a positive or negative mold. Indirect fabrication of an orthodontic appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

In some embodiments, the orthodontic appliances herein can be fabricated using a combination of direct and indirect fabrication techniques, such that different portions of an appliance can be fabricated using different fabrication techniques and assembled in order to form the final appliance. For example, an appliance shell can be formed by indirect fabrication (e.g., thermoforming), and one or more structures or components as described herein (e.g., auxiliary components, power arms, etc.) can be added to the shell by direct fabrication (e.g., printing onto the shell).

Methods of Design

Figure 2:
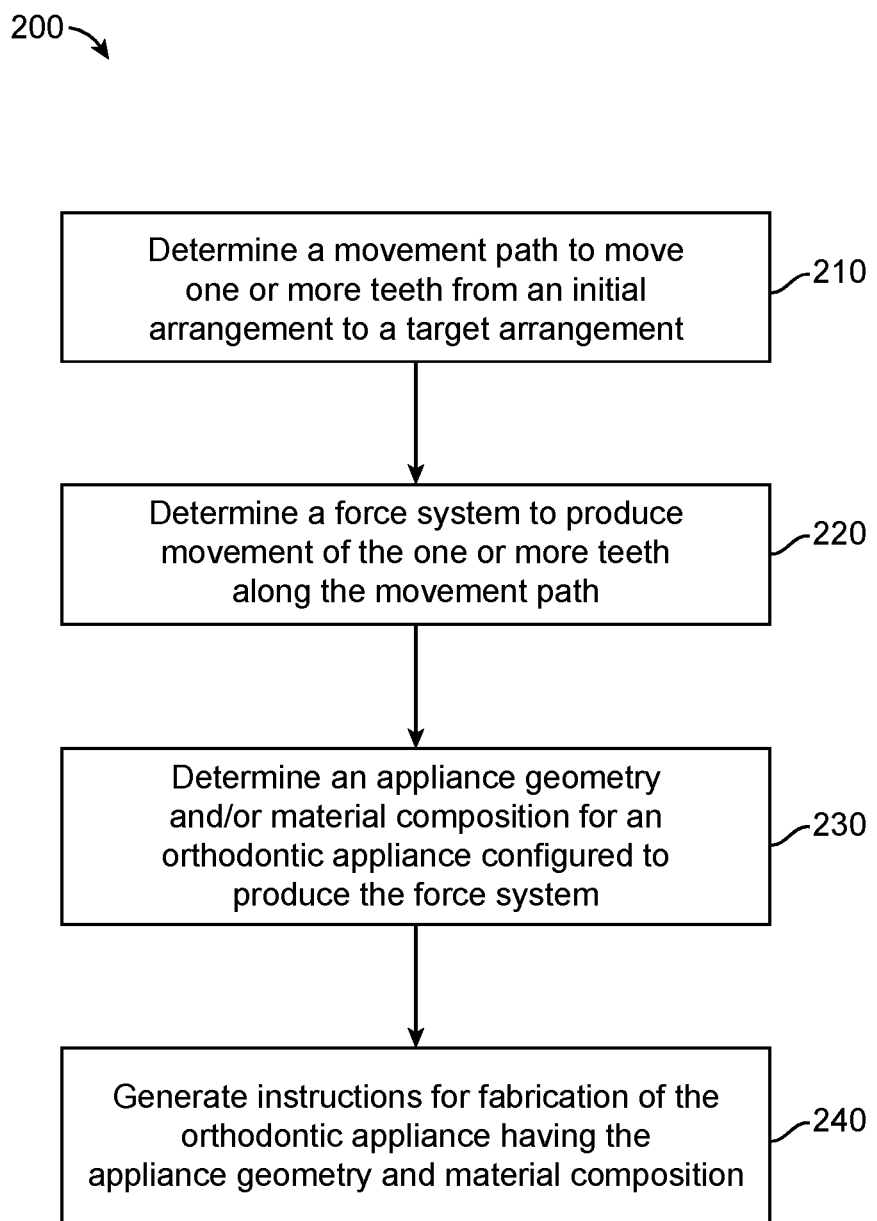
FIG. 2 illustrates a method for designing an orthodontic appliance, in accordance with one or more aspects of the methods disclosed herein.

FIG. 2 illustrates a method 200 for designing an orthodontic appliance to be fabricated, in accordance with embodiments. The method 200 can be applied to any embodiment of the orthodontic appliances described herein.

Some or all of the operations of the method 200 can be performed by any suitable data processing system or device, e.g., one or more processors configured with suitable instructions.

In block 210, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 220, a force system to produce movement of the one or more teeth along the movement path is determined. In some embodiments, the torque system may be determined. A moment system may be determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

Determination of the force system can be performed in a variety of ways. For example, in some embodiments, the force system is determined on a patient-by-patient basis, e.g., using patient-specific data. Alternatively or in combination, the force system can be determined based on a generalized model of tooth movement (e.g., based on experimentation, modeling, clinical data, etc.), such that patient-specific data is not necessarily used. In some embodiments, determination of a force system involves calculating specific force values to be applied to one or more teeth to produce a particular movement. Alternatively, determination of a force system can be performed at a high level without calculating specific force values for the teeth. For instance, block 220 can involve determining a particular type of force to be applied (e.g., extrusive force, intrusive force, translational force, rotational force, tipping force, torqueing force, etc.) without calculating the specific magnitude and/or direction of the force.

In block 230, an appliance geometry and/or material composition for an orthodontic appliance configured to produce the force system is determined. The appliance can be any embodiment of the appliances discussed herein, such as an appliance having variable localized properties, integrally formed components, and/or power arms.

For example, in some embodiments, the appliance comprises a heterogeneous thickness, a heterogeneous stiffness, or a heterogeneous material composition. In some embodiments, the appliance comprises two or more of a heterogeneous thickness, a heterogeneous stiffness, or a heterogeneous material composition. In some embodiments, the appliance comprises a heterogeneous thickness, a heterogeneous stiffness, and a heterogeneous material composition. The heterogeneous thickness, stiffness, and/or material composition can be configured to produce the force system for moving the teeth, e.g., by preferentially applying forces at certain locations on the teeth. For example, an appliance with heterogeneous thickness can include thicker portions that apply more force on the teeth than thinner portions. As another example, an appliance with heterogeneous stiffness can include stiffer portions that apply more force on the teeth than more elastic portions. Variations in stiffness can be achieved by varying the appliance thickness, material composition, and/or degree of photopolymerization, as described herein.

In some embodiments, determining the appliance geometry and/or material composition comprises determining the geometry and/or material composition of one or more integrally formed components to be directly fabricated with an appliance shell. The integrally formed component can be any of the embodiments described herein. The geometry and/or material composition of the integrally formed component(s) can be selected to facilitate application of the force system onto the patient's teeth. The material composition of the integrally formed component can be the same as or different from the material composition of the shell.

The block 230 can involve analyzing the desired force system in order to determine an appliance geometry and material composition that would produce the force system. In some embodiments, the analysis involves determining appliance properties (e.g., stiffness) at one or more locations that would produce a desired force at the one or more locations. The analysis can then involve determining an appliance geometry and material composition at the one or more locations to achieve the specified properties. Determination of the appliance geometry and material composition can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the Auto-CAD® software products available from Autodesk, Inc., of San Rafael, Calif. For creating finite element models and analyzing them, program products from a number of vendors can be used, including finite element analysis packages from ANSYS, Inc., of Canonsburg, Pa., and SIMULIA (Abaqus) software products from Dassault Systèmes of Waltham, Mass.

Optionally, one or more appliance geometries and material compositions can be selected for testing or force modeling. As noted above, a desired tooth movement, as well as a force system required or desired for eliciting the desired tooth movement, can be identified. Using the simulation environment, a candidate appliance geometry and composition can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

Optionally, block 230 can further involve determining the geometry of one or more auxiliary components to be used in combination with the orthodontic appliance in order to exert the force system on the one or more teeth. Such auxiliaries can include one or more of tooth-mounted attachments, elastics, wires, springs, bite blocks, arch expanders, wire-and-bracket appliances, shell appliances, headgear, or any other orthodontic device or system that can be used in conjunction with the orthodontic appliances herein. The use of such auxiliary components may be advantageous in situations where it is difficult for the appliance alone to produce the force system. Additionally, auxiliary components can be added to the orthodontic appliance in order to provide other desired functionalities besides producing the force system, such as mandibular advancement splints to treat sleep apnea, pontics to improve aesthetic appearance, and so on. In some embodiments, the auxiliary components are fabricated and provided separately from the orthodontic appliance. Alternatively, the geometry of the orthodontic appliance can be modified to include one or more auxiliary components as integrally formed components.

In block 240, instructions for fabrication of the orthodontic appliance having the appliance geometry and material composition are generated. The instructions can be configured to control a fabrication system or device in order to produce the orthodontic appliance with the specified appliance geometry and material composition. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.). In alternative embodiments, the instructions can be configured for indirect fabrication of the appliance, e.g., by thermoforming.

Although the above blocks show a method 200 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 200 may be performed with any suitable fabrication system or device, such as the embodiments described herein. Some of the blocks may be optional, and the order of the blocks can be varied as desired. For instance, in some embodiments, block 220 is optional, such that block 230 involves determining the appliance geometry and/or material composition based directly on the tooth movement path rather than based on the force system.

Treatment Planning

Figure 3:
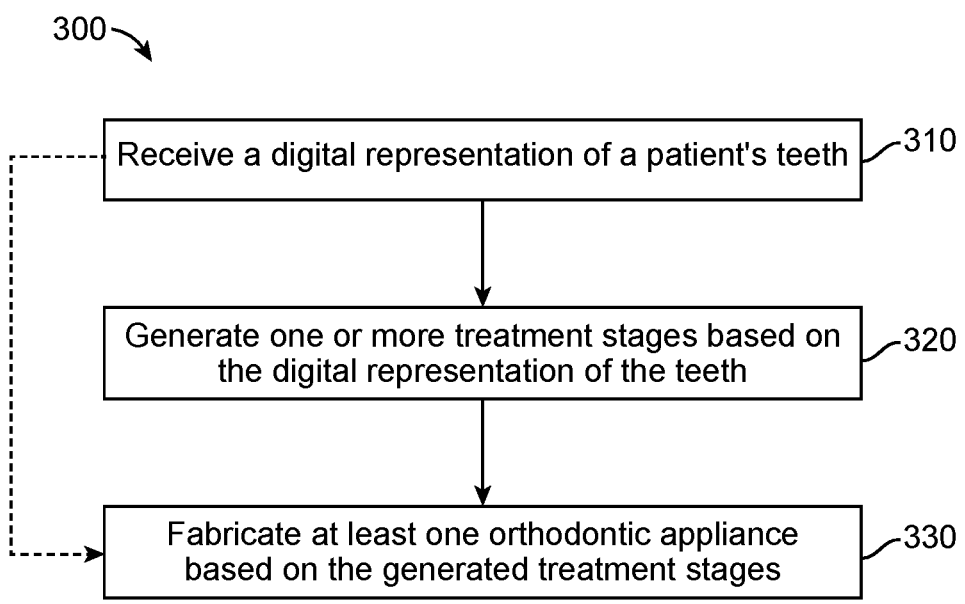
FIG. 3 illustrates a method for planning an orthodontic treatment, in accordance with one or more embodiments herein.

FIG. 3 illustrates a method 300 for digitally planning an orthodontic treatment and/or design or fabrication of an appliance, in accordance with embodiments. The method 300 can be applied to any of the treatment procedures described herein and can be performed by any suitable data processing system.

In block 310, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 320, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 330, at least one orthodontic appliance is fabricated based on the generated treatment stages. For example, a set of appliances can be fabricated, each shaped according to a tooth arrangement specified by one of the treatment stages, such that the appliances can be sequentially worn by the patient to incrementally reposition the teeth from the initial arrangement to the target arrangement. Each aligner may translate each tooth at most about 0.25 mm over a period from one to two weeks. Each aligner may rotate each tooth at most about 2 degrees over a period of time from 1 to 2 weeks. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 3, design and/or fabrication of an orthodontic appliance, and perhaps a particular orthodontic treatment, may include use of a representation of the patient's teeth (e.g., receive a digital representation of the patient's teeth 310), followed by design and/or fabrication of an orthodontic appliance based on a representation of the patient's teeth in the arrangement represented by the received representation.

Optionally, some or all of the blocks of the method 300 are performed locally at the site where the patient is being treated and during a single patient visit, referred to herein as "chair side manufacturing." Chair side manufacturing can involve, for example, scanning the patient's teeth, automatically generating a treatment plan with treatment stages, and immediately fabricating one or more orthodontic appliance(s) to treat the patient using a chair side direct fabrication machine, all at the treating professional's office during a single appointment. In embodiments where a series of appliances are used to treat the patient, the first appliance may be produced chair side for immediate delivery to the patient, with the remaining appliances produced separately (e.g., off site at a lab or central manufacturing facility) and delivered at a later time (e.g., at a follow up appointment, mailed to the patient). Alternatively, the methods herein can accommodate production and immediate delivery of the entire series of appliances on site during a single visit. Chair side manufacturing can thus improve the convenience and speed of the treatment procedure by allowing the patient to immediately begin treatment at the practitioner's office, rather than having to wait for fabrication and delivery of the appliances at a later date. Additionally, chair side manufacturing can provide improved flexibility and efficiency of orthodontic treatment. For instance, in some embodiments, the patient is re-scanned at each appointment to determine the actual positions of the teeth, and the treatment plan is updated accordingly. Subsequently, new appliances can be immediately produced and delivered chair side to accommodate any changes to or deviations from the treatment plan.

Appliance Modeling

In some embodiments, the present disclosure provides systems and methods which improve a computational time to model a stage or a series of stages in a treatment plan. In some cases, the method may be used to model a treatment plan. The method may reduce the number of optimized parameters over models based on finite element analysis. Methods and systems may make approximations in order to reduce computational cost. In some embodiments, the present disclosure provides for designing an orthodontic appliance to be fabricated.

Figure 4:
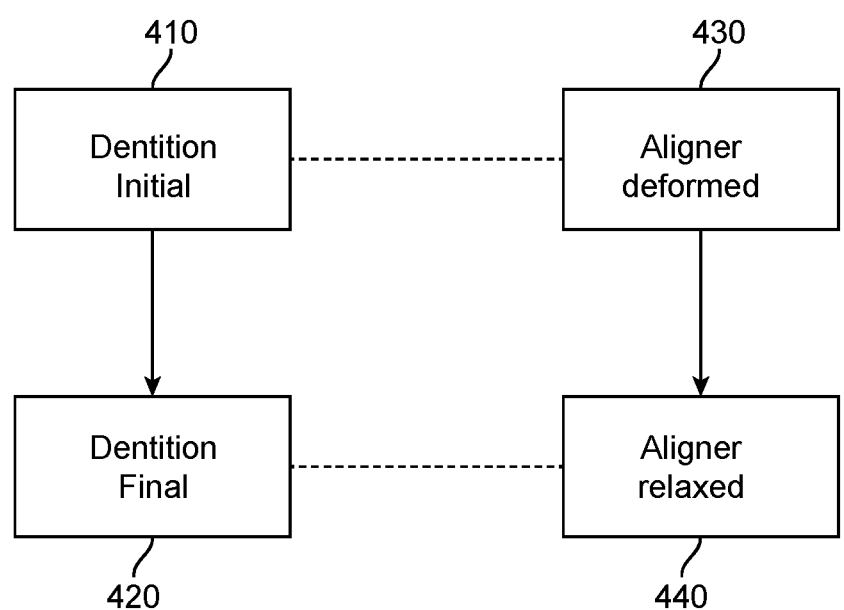
FIG. 4 shows a relationship between the initial and final representation of the patient dentition and the relaxed and deformed model of the aligner, in accordance with one or more embodiments herein.

FIG. 4 shows a relationship between the initial and final representation of the patient dentition and the relaxed and deformed model of the aligner, in accordance with some embodiments. The initial 410 and final 420 representation may relate to the position of the patient teeth, while the deformed 430 and relaxed models 440 may relate to the configuration of the aligner. Before a stage in a treatment plan, the patient dentition may be in an initial configuration, and the aligner may be significantly deformed when is inserted in the patient mouth. Over time, the aligner may relax as the teeth move in response to the force on the teeth generated by the aligner. After a stage in the treatment plan, the aligner may comprise a relaxed or a more relaxed geometry than at the beginning of the stage in the treatment plan. In order to produce an effective aligner, it may be beneficial to know the magnitude and direction of forces and moments to apply to the patient's teeth.

Figure 5A:
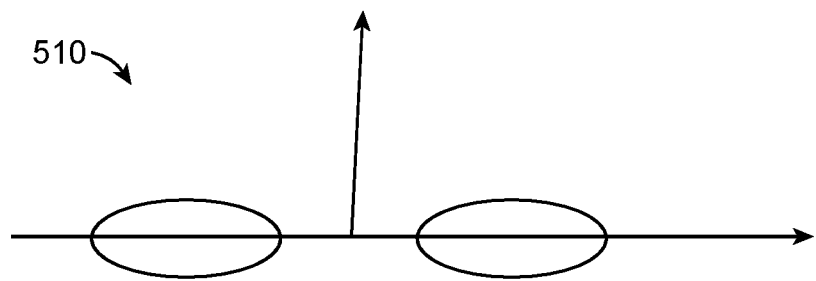
FIG. 5A shows a simplified schematic rendering of two sets two caps each joined by a link, in accordance with one or more embodiments herein.
Figure 5A:
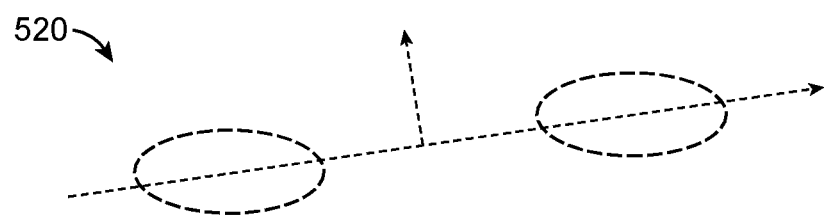

FIG. 5A shows a simple schematic rendering of two sets two caps each joined by a link. In some embodiments, the caps may be an abstraction of a tooth receiving cavity, representing physical properties, such as their position, orientation, shape, etc. in two or three dimensional space. In some embodiments, the cap may comprise a reduced dimensional surface representing the shape of an individual tooth. In some cases, the shape of a tooth may be approximated by a cylinder or an elliptic cylinder. The cap may be a rigid body that may translate and rotate within the model. The cap may represent a contact point on a tooth of the dentition. In some cases, the shape of the tooth may be approximated from three-dimensional rendering of a tooth from a finite element analysis model. The shape of the tooth may be approximated by a finite element analysis model with a minimal or reduced discretization of the surface. For example, the cap may be approximated by a lower fidelity finite element model than is used to manufacture an aligner. The fidelity of the model may be reduced to decrease computational cost of a model of the force/moment system of the patient dentition. In some cases, the cap may approximate the same contour or shape of the tooth. In some cases, deformations in the shape of the cap may not be considered in the deformed model. In some cases, only small deformations in the shape of the cap may be considered.

The link may be an abstraction that represents the aligner material that makes up and connects two tooth receiving cavities, represented by caps. A link may represent a connection between two of the plurality of caps. In some cases, the link may connect two adjacent caps. In some cases, the link may connect to caps which are not adjacent. In some cases, the link may be approximated by line segment connecting the caps. The link to be used in the relaxed and deformed model may comprise a Hookian stiffness parameter. The Hookian stiffness parameter may represented by a constant with distance. In some cases, the stiffness parameter may be represented by a higher order polynomial, for example, a quadratic, a third order polynomial, or higher. In some cases, the stiffness parameter may be represented by a matrix comprising a different stiffness parameter in each spatial dimension. In some cases, the link may be approximated by a finite element analysis model with a minimal or reduced discretization of the surface. For example, the link may be approximated by a lower fidelity finite element model than is used to manufacture an aligner. The fidelity of the model may be reduced to decrease computational cost of a model of the force/moment system of the patient dentition.

In some embodiments, a relaxed model may be generated. In some examples the method may comprise generating a relaxed model of a dental appliance from the plurality of caps and the plurality of links. The relaxed model may represent an arrangement of caps and links which relates to the representation of the patient dentition after a stage of the treatment plan or of aligner. The tooth receiving cavities may be arranged to impart a tooth moving force on one or more teeth of the patient. Before the appliance is attached to a patient jaw, the appliance may be in a configuration that relates to the relaxed model of the aligner. Before application of the appliance on the patient teeth, the appliance may be in a relaxed and original manufactured shape. Before the application of the appliance on the patient teeth, the positions of the caps may be in relaxed positions.

In some embodiments, a deformed model may be generated. In some examples the method may comprise generating a deformed model of a dental appliance from the plurality of caps and plurality of links. The deformed model may represent an arrangement of caps and links which relates to the representation of the patient dentition before a stage of the treatment plan. After the appliance is attached to a patient's arch and before progression of tooth movement, the appliance may be in a configuration that relates to the deformed model of the aligner. After application of the appliance on the patient teeth, the appliance may be in a deformed shape. The degree to which the appliance may be deformed may change as a function of time and as the teeth move. In some cases, the position of the deformed caps may be the same as the teeth positions, such as if the fit is perfect.

In some cases, the position of the deformed caps may also be different. Such effect may be limited by the stiffness and/or compliance of the appliance material. After the application of the appliance on the patient teeth, the positions of the caps may be in the deformed position.

FIG. 5A shows an example of relaxed 510 and deformed 520 cap positions in a model of dentition comprising two teeth. In some embodiments, an elastic coordinate system may be defined. As shown in the illustrated embodiment, the elastic coordinate of for each of the relaxed and deformed positions is indicated by the arrows. In some embodiments, a relaxed model and a deformed model of the aligner may be defined.

In some embodiments, a coordinate system based on the center of the pair of caps may be defined. If the pair is moved together, the position of each tooth relative to the center coordinate system may be unchanged. Such a coordinate system may be called the elastic coordinate C. The elastic coordinate origin may be at the center of two caps: $C=(C_1+C_2)/2$, where $C_1$, $C_2$ may be the center of each cap of each of the two teeth. In some cases, Y may be the distance (mesial/distal) direction of two teeth: $y=(C_2-C_1)$, and X may be the buccal-lingual direction of two teeth and related to Y by $x=y \times (\hat{z}_1+\hat{z}_2)/2$. Finally, Z may be the extrusion direction of two teeth and $z=x \times y$.

Figure 5B:
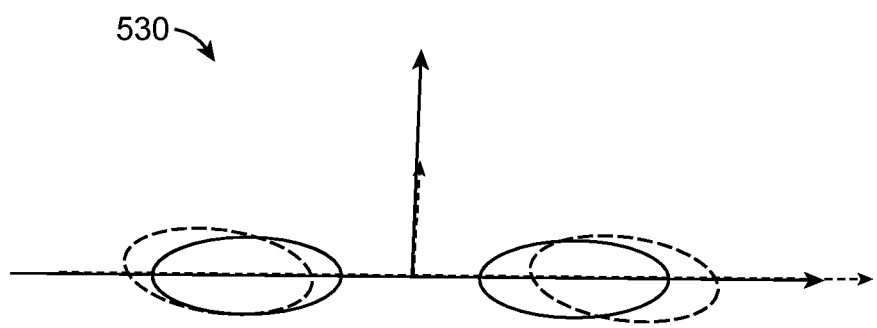
FIG. 5B shows a pair of exemplary caps whose relaxed and deformed coordinates have been mapped together, in accordance with one or more embodiments herein.

FIG. 5B shows a pair of exemplary caps 530 whose relaxed and deformed coordinates have been mapped together. In some cases, the method may comprise mapping the relaxed coordinate to the deformed coordinate. In some cases, the relaxed coordinate may have the same center as the deformed coordinate. After transformation, the relaxed coordinate may have the same axes as the deformed coordinate. Mapping the relaxed coordinate onto the deformed coordinate may assure that there is no total displacement or rotation force on the arch.

In some embodiments, a plurality of transformational parameters may be determined. The transformational parameters may comprise a plurality of moments and/or a plurality of forces associated with the caps. In some embodiments, the force and moment between any two neighboring caps may be nonlinearly related to the translational and rotational movement. The nonlinear parts may include but are not limited to the cross products of the rotation vector and the distance vector between two teeth or the teeth direction. A force system can include one or more forces and/or one or more torques. Different force systems can result in different types of tooth movement, such as tipping, translation, rotation, extrusion, intrusion, root movement, etc. Determination of the force system can be performed in a variety of ways. For example, in some embodiments, the force system is determined on a patient-by-patient basis, e.g., using patient-specific data.

In some embodiments, the forces and/or moments may be determined for each pair of teeth connected by a link. The forces for each pair may then be summed in order to generate a model of the whole jaw or whole arch system. A reduced model of the forces and/or moments on each tooth may comprise forming pairs of neighboring caps. Each two neighboring caps may be connected by their links. The moment may be obtained from the sum of all the pairs. The total force and/or moment may be defined as sum of forces and/or moments of all pairs. Without being limited by theory, if the appliance as a whole is moved, there should be no force on the pair. If the appliance as a whole is moved either by rotating or translating the appliance as a whole, there should be no force on the pair.

As shown in FIG. 5B, after mapping the relaxed and deformed coordinate onto one another, each tooth may be individually rotated or displaced from relaxed to deformed. The difference between the relaxed and deformed position of the first cap may be defined as $(\theta_1, T_1)$, where $\theta_1$ may be the rotation angle for each axis for the first cap from the deformed to relaxed orientation and where $T_1$ may be the translation of the first cap from the deformed to relaxed position. The rotation matrix or quaternion $Q$ may then be defined as follows:

$$(\theta_1, T_1) \sim Q(\theta_1), T_1) = (Q(\theta_{1R})Q(\theta_{1D})^{-1}, T_{1R}T_{1D}).$$

Similarly for the second cap, the difference may be defined as $(\theta_2, T_2)$ where $\theta_2$ may be the rotation angle for each axis for the first cap from the deformed to relaxed orientation and where $T_2$ may be the translation of the first cap from the deformed to relaxed position. The convention above may move the negative sign in Hooke's law into the difference.

In the illustrated embodiment, only a translation in the medial-distal direction, Ty, survives, which may be represented as follows:

$$Tx=0, Tz=0, T_{1y}=-T_{2y}.$$

Therefore, the force in the medial-distal direction may be represented as:

$$F_{1y}=\alpha(T_{1y}-T_{2y})=2\alpha T_{1y}=-F_{2y}.$$

In the illustrated embodiment, there is no net moment from translation (i.e. each tooth moves in an equal and opposite direction). In the example, the number of translation coordinates may be reduced as $T_x$ and $T_z$ are replaced by two teeth with equal rotation plus a small $T_y$.

In some examples, the method may comprise determining a plurality of moments, wherein the plurality of moments transform the relaxed model to the deformed model and wherein the moments are configured to direct the patient dentition from the initial model to the target model. In an example, one may consider a case where there may be only $\theta_1$, moment on $T_1$ and $T_2$. In such as case, the rotational moment may be defined by the following:

$$M_{11}^L = \beta \theta_1, M_{21}^L = -\beta \theta_1,$$

where $\beta$ is 3×3 matrix relating the magnitude of the rotation, which may be mainly diagonal (3 Params). Alternatively, in an example case where there may be only $\theta_2$, the moment on $T_1$ and $T_2$ may be defined as $M_{22}^L=\beta\theta_2$, $M_{12}^L=-\beta\theta_2$. In cases where there may be non-zero $\theta_1$, $\theta_2$, the moment may be:

$$M_1^L=\beta(\theta_1-\theta_2), M_2^L=\beta(\theta_2-\theta_1).$$

From the moment, the linear part of the rotation force may be defined. For a case with both $\theta_1$, $\theta_2$, the force may be:

$$F_1^L=\psi(\theta_1-\theta_2), F_2^L=\psi(\theta_2-\theta_1),$$

where $\psi$ is a 3×3 stiffness matrix. The largest components to the stiffness matrix may be xy and yx. In some embodiments the force pair may be balanced. In some cases an extra moment may be defined to balance the force pair, which may be defined as:

$$M_1'^L = M_2'^L = \psi(\theta_1 - \theta_2) \times \frac{y_{12}}{2}.$$

When $\theta_1=\theta_2$, all linear parts may be zero. Translations in X and Z may require a nonzero linear term.

In a first example, the cross product of the force in the medial-distal direction may be quadratic. In some embodiments, the rotation force may be quadratic. In an example, the force may be F=γ(θ×y), where y is distance vector of two teeth. The direction of F may be quadratic of two vector (θ, y), its magnitude may linear in R, and y may be a 3×3 stiffness matrix. In some cases, γ may be diagonal, and there may be zero $F_y$, but non-zero $F_x$ and $F_z$. The cross product of the medial-distal force may have a similar effect of the horizontal beam rotation (xz, zx).

In some cases, the total tooth rotation force may have components for each tooth and coupling components. For rotation of tooth 1, by Newton's $3^{rd}$ law the force may be:

$F_{11}=\gamma(\theta_1 \times y_{12})$, and $F_{21}=-\gamma(\theta_1 \times y_{12})$.

For rotation of tooth 2, similarly the force may be:

$F_{22}=\gamma(\theta_2 \times y_{21}), F_{12}=-\gamma(\theta_2 \times y_{21})=\gamma(\theta_2 \times y_{12})$ The total force on tooth 1 may then be:

$F_1=\gamma((\theta_1+\theta_2) \times y_{12})$, and the total force on tooth 2 may be:

$F_2=-F_1=-\gamma((\theta_1+\theta_2) \times y_{12})$.

For the case of one tooth pair, because the total moment is zero, $$M_1' = M_2' = M' = F_2 \times \frac{y_{12}}{2} = -\gamma/2(\theta_1+\theta_2) \times y_{12} \times y_{12}.$$

In the illustrated example, the cross product of the force in the extrusion direction may be quadratic. Based on the defined axes, $\theta_x$ gives $F_y$, and $\theta_y$ gives $F_x$, and they are opposite for the teeth of lower and upper jaws with the same rotation. The translation in the extrusion direction may not be represented by a linear model. Instead, the translation may be represented by θ×z for both $\theta_1$ and $\theta_2$. In the illustrated embodiment, the force may be represented as:

$F_1^C=\psi((\theta_1-\theta_2) \times z)=-F_2^L$, where ψ is a 3×3 stiffness diagonal matrix. In order to balance the force pair, another moment may be defined as:

$$M_1^C = M_2^C = \psi((\theta_1-\theta_2) \times z) \times \frac{y_{12}}{2}.$$

As shown, if $\theta_1=\theta_2$, the moment goes to zero.

To arrive at the total force, the forces on each teeth may be summed together, such that $F_1=2\alpha T_{1y}\hat{y}+\gamma((\theta_1+\theta_2) \times y_{12})+\psi((\theta_1-\theta_2) \times z)$, and because $F_2=-F_1$. The total moment may then be expressed as:

$$M_1^L = \beta(\theta_1-\theta_2) - \gamma/2(\theta_1+\theta_2) \times y_{12} \times y_{12} + \psi((\theta_1-\theta_2) \times z) \times \frac{y_{12}}{2}, \text{ and}$$

$$M_2^L = \beta(\theta_2-\theta_1) - \gamma/2(\theta_1+\theta_2) \times y_{12} \times y_{12} + \psi((\theta_1-\theta_2) \times z) \times \frac{y_{12}}{2}.$$

Modeling Tooth Moments

Figure 6:
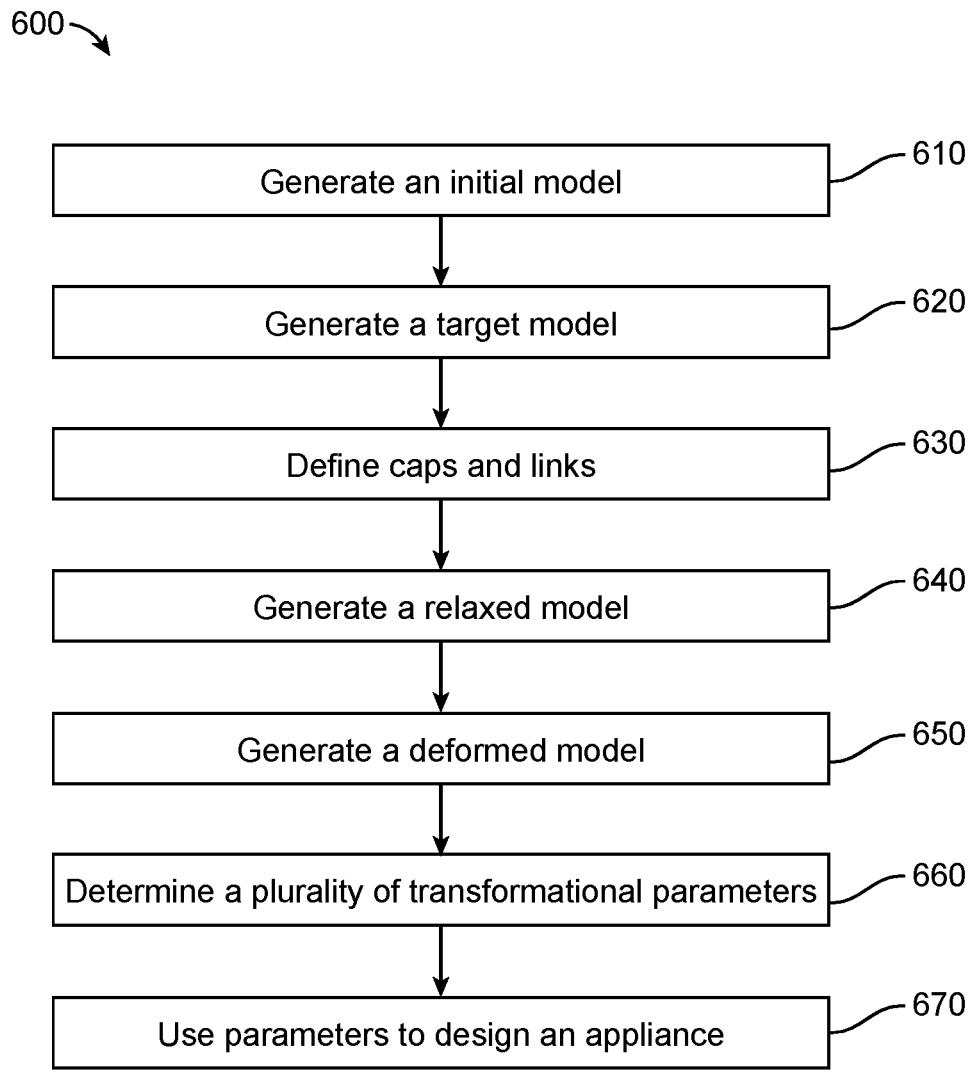
FIG. 6 illustrates a method for orthodontic modeling of tooth forces and/or moments, in accordance with one or more embodiments herein.

FIG. 6 illustrates a method 600 for orthodontic modeling of tooth movements. In some embodiments, the method 600 may comprise a portion of block 220 of a method 200. In other embodiments, the method 600 may be used to model a plurality of treatment stages and a plurality of treatment plans in order to determine an effectiveness of a treatment plan. In some cases, the method 600 may be applied as an operation in a method of digitally planning an orthodontic treatment method as described elsewhere herein. The method 600 may be applied to any of the treatment procedures described herein and may be performed by a suitable data processing system, such as for example the data processing system described in the section titled "Digital Processing System".

In block 610 of the method 600, an initial representation of the patient dentition may be generated. The initial representation of the patient dentition may comprise the arrangement of teeth before a stage in a treatment plan. In some embodiments, the initial representation may comprise the arrangement of teeth before starting a treatment plan. Systems and methods provided herein may comprise one or more representations of a patient dentition. A patient dentition may comprise an arrangement of teeth in a patient mouth. The arrangement of teeth may comprise the shape, location, morphology, number type, and/or physiological properties of one or more patient teeth. Dental information as described herein may comprise a patient dentition. A representation of a patient dentition may comprise an image of the patient's teeth. The image may be two-dimensional or three-dimensional.

The representation of the patient dentition before beginning treatment may be generated from a mold the patient's dental arch. For example, a practitioner (e.g. a dentist, an orthodontist, a technician, etc.) may make an impression of the subject's teeth and gingiva. Impressions may comprise impressions of the upper and/or the lower jaw. The impressions may be prepared using standard techniques, such as a dental tray filled with polyvinylsiloxane. The mold of the patient arch may then be scanned in order to generate a digital representation of the patient dentition.

The initial representation can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues.

In some cases, the teeth may be scanned or measured to determine the position of the teeth. Any appropriate technique may be used to scan the patient mouth. Such methods may include manual measurement, contact scanning, and non-contact scanning. Contact scanning may comprise actual or computer assisted measurement, including mechanical location devices. The teeth may be scanned by a non-contact method. In some examples, a non-contact method may comprise, but are not-limited too, laser scanning, optical scanning, CT scanning, ultrasound scanning, X-ray scanning, etc.

In some cases, multiple scanning steps may be combined in order to create a representation of the patient dentition. In some cases, multiple X-ray scans may be combined; multiple ultrasound scans, and/or multiple CT scans may be combined. In some cases, images may be digitized and/or analyzed to create a three dimensional representation of the patient dentition. The model may comprise a tomographic image of the patient dentition.

The scanning device may be coupled to a computer (e.g. a processor, a digital processing device, etc) as described elsewhere herein. Dental information, such as position and orientation for one or more of the patient teeth, may be obtained based on the scan of the patient mouth. The position and orientation information may be stored, analyzed, processed, and/or obtained from the scanner by the computer. The computer may act as a controller. The computer may comprise a plurality of computers which may be remote to one another each configured to execute one or more steps of the method described herein.

The dental information including the patient dentition may be collected over time, for example at each stage of a treatment plan. The position and orientation of the patient teeth may be recorded over time. The dental information may be used to assess the progress of a patient treatment plan. The dental information may be used to develop a patient treatment plan; however, in some cases, a patient treatment plan may be provided by another method.

In block 620 of the method 600, a target representation of the patient dentition may be generated. A target three dimensional representation may be generated. In some cases, the target representation comprises the target position of one or more patient teeth after a stage in the treatment plan. In some cases, the target dentition comprises the target arrangement of a patient teeth after the completion of a treatment plan. The treatment plan may be developed from a method described herein. Alternatively, the treatment plan may be provided from another method. In some cases, the treatment plan may be provided by a practitioner. The treatment plan may comprise one or a plurality of steps configured to adjust the alignment of the patient dentition toward a target arrangement. In some cases, the configuration of the orthodontic appliances herein can be determined according to a treatment plan for a patient, e.g., a treatment plan involving successive administration of a plurality of appliances for incrementally repositioning teeth.

The target representation may comprise the desired position of teeth at the end of a stage in a treatment plan. In some cases, the method includes a plurality of initial representations and target representations each representing the teeth at the beginning and end of a treatment stage in the treatment plan. In some examples, the treatment plan comprises greater than two stages. In some examples, the treatment plan comprises greater than 5 stages, greater than 10 stages, greater than 20 stages, greater than 100 stages or more. In some examples, the number of stages may be within a range defined by any two of the preceding values. In some cases the plurality of initial and final representations may be equal to the number of stages. The number of relaxed and deformed models may be equal to the number of stages in a treatment plan.

In some examples, computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled additive manufacturing such as 3D printing, etc.). In some embodiments, computer-based 3D planning/design tools, such as Treat™ software from Align Technology, Inc., may be used to design and fabricate the orthodontic appliances described herein.

At a block 630 of the method 600, a plurality of caps and a plurality of links may be defined. An operation in the method of modeling tooth moments may include separating each representation of the patient dentition into individual teeth. In some embodiments, each tooth has its own three-dimensional position and orientation. Each cap may represent a set of contact points on a tooth of the dentition. In some cases, each tooth may comprise a single cap. In some cases, a cap may represent more than one tooth. Two teeth may be represented with a single cap. Three teeth may be represented with a single cap. Each link may represent a connection between two of the caps. Each link may represent a connection between two adjacent caps. In other examples, each link may connect two non-adjacent caps. In some examples, the method may comprise defining a cap position and orientation for each tooth and a link, where each link connects neighboring adjacent caps. The plurality of caps and the plurality of links may define an aligner force response based on aligner deformation. The plurality of caps and plurality of links may represent the full patient dentition. In some cases, the plurality of caps and plurality of links may represent a portion of the patient dentition, for example, an upper arch, a lower arch, etc. In some cases, the plurality of caps and the plurality of links may represent only a portion of an arch.

At a block 640 of the method 600, a relaxed model may be generated. In some examples the method may comprise generating a relaxed model of a dental appliance from the plurality of caps and the plurality of links. The relaxed model may represent physical properties of the appliance at a first state. The first state may be an initial state. The relaxed model may represent the dental appliance. The relaxed model may represent the dental appliance in a first state. The relaxed model may represent an arrangement of caps and links which relates to the representation of the patient dentition after a stage of the treatment plan. Before the appliance is attached to a patient jaw, the appliance may be in a configuration that relates to the relaxed model of the aligner. Before application of the appliance on the patient teeth, the appliance may be in a relaxed and original manufactured shape. Before the application of the appliance on the patient teeth, the positions of the caps may be in relaxed positions.

At a block 650 of the method 600, a deformed model may be generated. In some examples the method may comprise generating a deformed model of a dental appliance from the plurality of caps and plurality of links. The deformed model may represent physical properties of the appliance at a second state. The second state may be a final state or an intermediate state. The second state may correspond to use of the dental appliance. The deformed model may represent the dental appliance. The deformed model may represent the dental appliance in a second state, for example, a state of the dental appliance in use. The deformed model may represent an arrangement of caps and links which relates to the representation of the patient dentition before a stage of the treatment plan. After the appliance is attached to a patient jaw and before progression of tooth movement, the appliance may be in a configuration that relates to the deformed model of the aligner. After application of the appliance on the patient teeth, the appliance may be in a deformed shape. The degree to which the appliance may be deformed may change as a function of time and as the teeth move. In some cases, the position of the deformed caps may be the same as the teeth positions, such as if the fit is perfect. In some cases, the position of the deformed caps may also be different by a bit, which effect may be limited by the stiffness and/or compliance of the appliance material. After the application of the appliance on the patient teeth, the positions of the caps may be in the deformed position.

At a block 660 of the method 600, a plurality of transformational parameters may be determined. The plurality of transformation parameters may comprise one or more of a plurality of forces and a plurality of moments. The plurality of transformational parameters may direct a patient dentition from the initial model to the target model. In some embodiments, the transformational parameters may comprise one or more forces. In some embodiments, the transformational parameters may comprise one or more moments. The transformation parameters may comprise forces and moments. The plurality of transformation parameters may relate to forces and moments for each tooth. In some embodiments, the force and moment between any two neighboring caps may be nonlinearly related to the translational and rotational movement. The nonlinear parts may include but are not limited to the cross products of the rotation vector and the distance vector between two teeth or the teeth direction. A force system can include one or more forces and/or one or more torques. Different force systems can result in different types of tooth movement, such as tipping, translation, rotation, extrusion, intrusion, root movement, etc. Determination of the force system can be performed in a variety of ways. For example, in some embodiments, the force system is determined on a patient-by-patient basis, e.g., using patient-specific data.

At a block 670 of the method 600, the plurality of dental parameters may be used to design a dental appliance. Having a set of moments and forces for the motion of each tooth, an appliance may be generated which produces or approximates the production of the calculated force. In some embodiments, the aligner tooth receiving cavities are in positions and orientations that correspond to the position and orientation of the caps in the model. In some embodiments, the motions and forces are configured to move the teeth in the quickest fashion with the least amount of round-tripping to bring the teeth from their initial positions to their desired target positions. In this way, the stage can constitute a clinically viable repositioning, and the aggregate of stages can constitute a clinically viable sequence of tooth positions.

In some embodiments, an appliance geometry and/or material composition for an orthodontic appliance configured to produce the force system may be determined. The appliance can be any embodiment of the appliances discussed herein, such as an appliance having variable localized properties, integrally formed components, and/or power arms.

Although the above blocks show a method 600 of orthodontic modeling of tooth movements in accordance with some embodiments, a person of ordinary skill in the art will recognize some variations based on the teaching described herein. Some of the blocks may comprise sub-blocks. Some of the blocks may be repeated as often as desired. One or more blocks of the method 600 may be performed with any suitable fabrication system or device, such as the embodiments described herein. Some of the blocks may be optional, and the order of the blocks can be varied as desired.

In some embodiments, the method 600 may be used for optimizing the predictability of patient treatment. The method may be used to predict mesial distal root control. The method may be used to predict optimized treatment plans with less processing power. The method may be used be used to predict the viability of a treatment plan. The method may be used to evaluate the progress of a treatment plan. The method may be used to approximate force values which may be more easily manufactured, such as for example, optimizing material properties in multi-material direct manufacturing.

Digital Processing System

Figure 7:
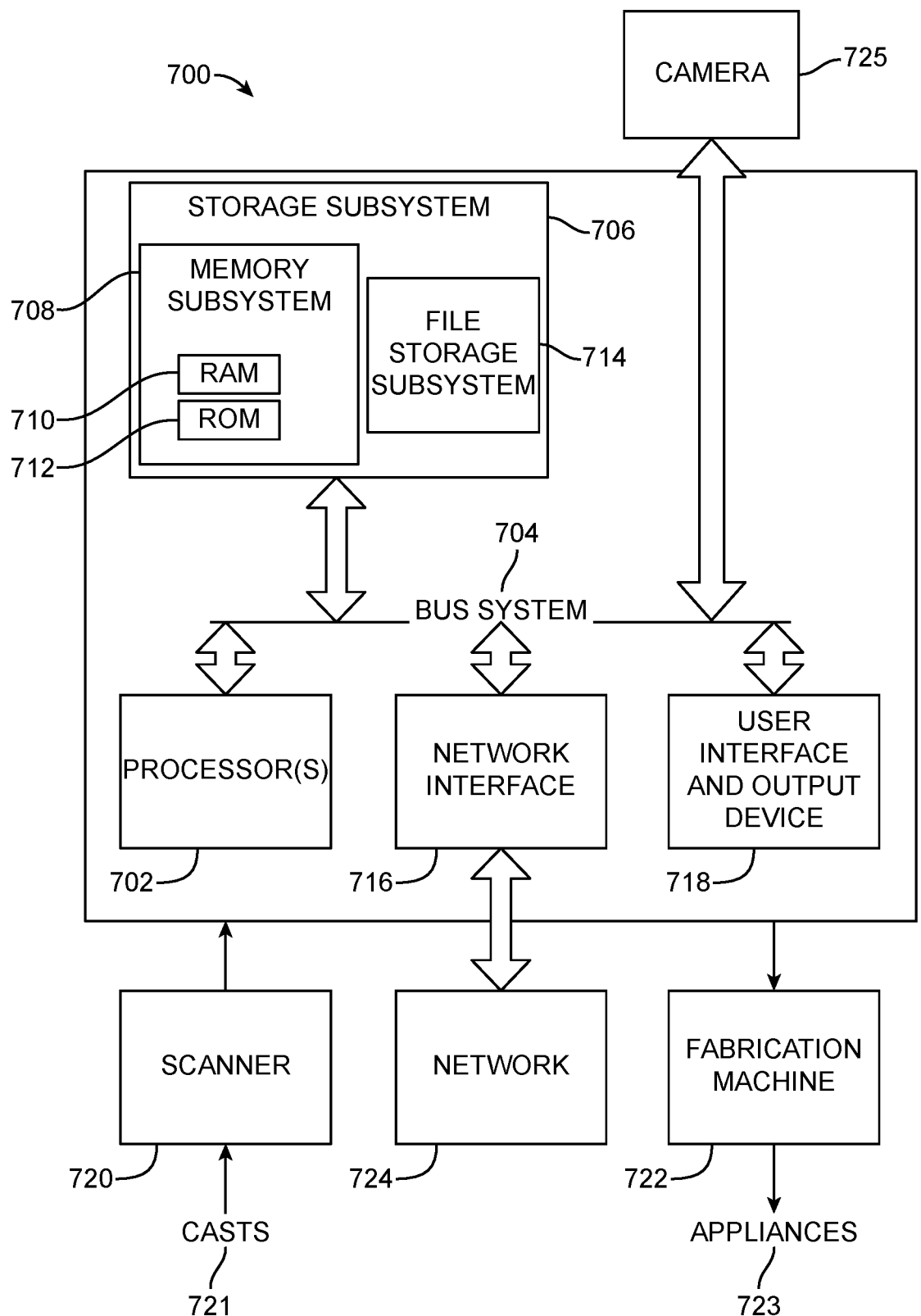
FIG. 7 is a simplified block diagram of a system for designing an orthodontic appliance and planning an orthodontic treatment, in accordance with one or more embodiments herein.

FIG. 7 is a simplified block diagram of a data processing system 700 that may be used in executing methods and processes described herein. The data processing system 700 typically includes at least one processor 702 that communicates with one or more peripheral devices via bus subsystem 704. These peripheral devices typically include a storage subsystem 706 (memory subsystem 708 and file storage subsystem 714), a set of user interface input and output devices 718, and an interface to outside networks 716. This interface is shown schematically as "Network Interface" block 716, and is coupled to corresponding interface devices in other data processing systems via communication network interface 724. Data processing system 700 can include, for example, one or more computers, such as a personal computer, workstation, mainframe, laptop, and the like.

The user interface input devices 718 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically includes memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk, CD-ROM, DVD, optical drives, and the like. One or more of the storage systems, drives, etc., may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining a digital representation (e.g., images, surface topography data, etc.) of a patient's teeth (e.g., by scanning physical models of the teeth such as casts 721, by scanning impressions taken of the teeth, or by directly scanning the intraoral cavity), which can be obtained either from the patient or from treating professional, such as an orthodontist, and includes means of providing the digital representation to data processing system 700 for further processing. Scanner 720 may be located at a location remote with respect to other components of the system and can communicate image data and/or information to data processing system 700, for example, via a network interface 724. Fabrication system 722 fabricates appliances 723 based on a treatment plan, including data set information received from data processing system 700. Fabrication machine 722 can, for example, be located at a remote location and receive data set information from data processing system 700 via network interface 724. The camera 725 may include any image capture device configured to capture still images or movies. The camera 725 may facilitate capturing various perspectives of a patient's dentition. In some implementations, the camera 725 may facilitate capture of images at various focal lengths and distances from the patient.

The data processing aspects of the methods described herein can be implemented in digital electronic circuitry, or in computer hardware, firmware, software, or suitable combinations thereof. Data processing apparatus can be implemented in a computer program product tangibly embodied in a machine-readable storage device for execution by a programmable processor. Data processing blocks can be performed by a programmable processor executing program instructions to perform functions by operating on input data and generating output. The data processing aspects can be implemented in one or more computer programs that are executable on a programmable system, the system including one or more programmable processors operably coupled to a data storage system. Generally, a processor will receive instructions and data from a read-only memory and/or a random access memory. Storage devices suitable for tangibly embodying computer program instructions and data include all forms of nonvolatile memory, such as: semiconductor memory devices, such as EPROM, EEPROM, and flash memory devices; magnetic disks such as internal hard disks and removable disks; magneto-optical disks; and CD-ROM disks.

Examples

The following examples show exemplary use cases for the methods disclosed herein. While examples, shown using 2, 3, or 4 teeth, the model may be extended to full arch modeling as described elsewhere herein.

Two Teeth with Equal Rotation

Figure 8:
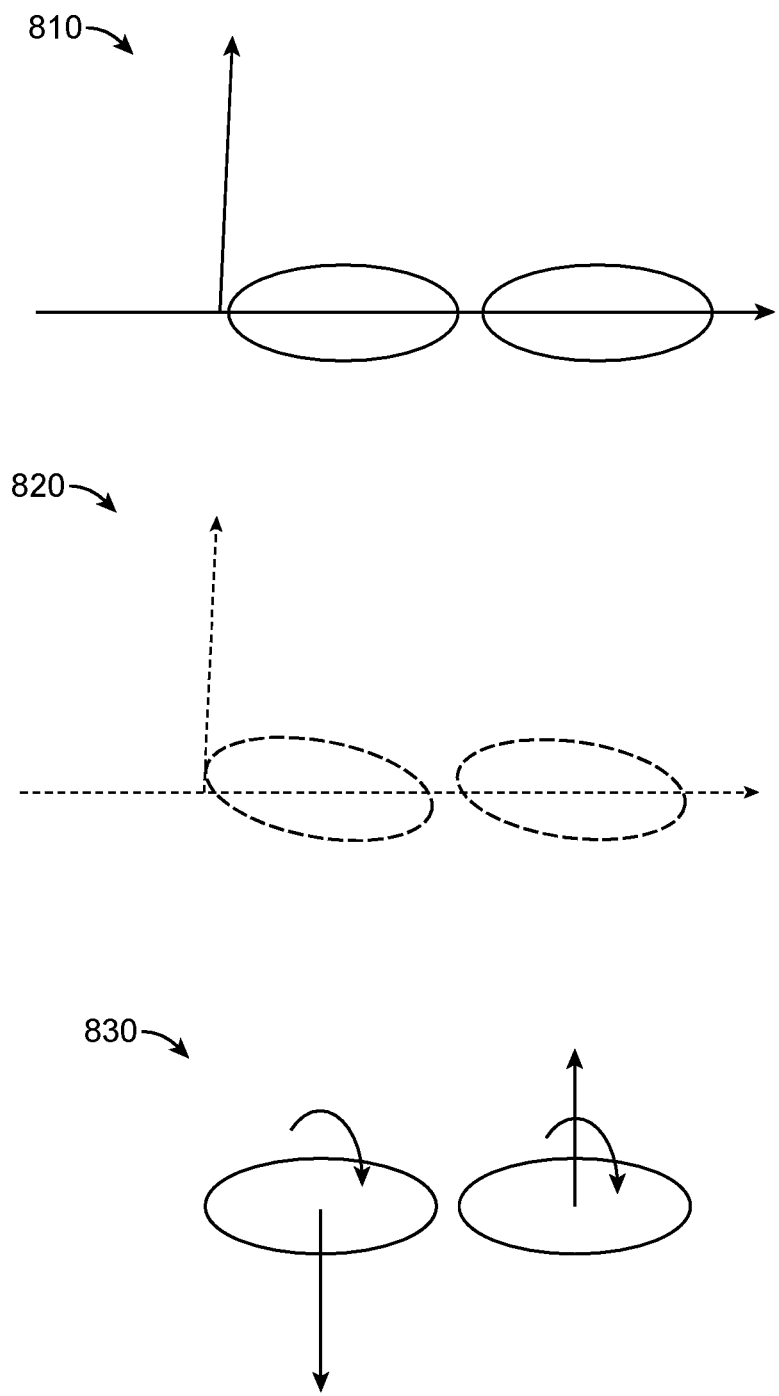
FIG. 8 illustrates an example of a moment model of a pair of teeth with equal rotation, in accordance with one or more embodiments herein.

FIG. 8 illustrates an example of a moment model of a pair of teeth with equal rotation. The relaxed model 810 is shown, and the deformed model 820 is shown. Similar to the embodiment shown herein above, the linear parts may all be zero. By definition, $\theta_{2z}=\theta_{1z}=\theta_z$, and the distance between the two teeth is y. The quadratic parts may then be expressed as:

$$F_{1x}=-F_{2x}=-\gamma 2\theta_z y.$$

The moments may be expressed as:

$$M'_{1z} = M'_{2z} = -\frac{\gamma}{2}(\theta_1 + \theta_2) \times y_{12} \times y_{12} = \gamma \theta_z y^2.$$

$\theta_x$ may be expressed similarly. A force diagram 830 is shown. The arrows indicate the direction of the forces, straight arrows, and moments, curved arrows on each tooth.

Three Teeth with Equal Rotation

Figure 9A:
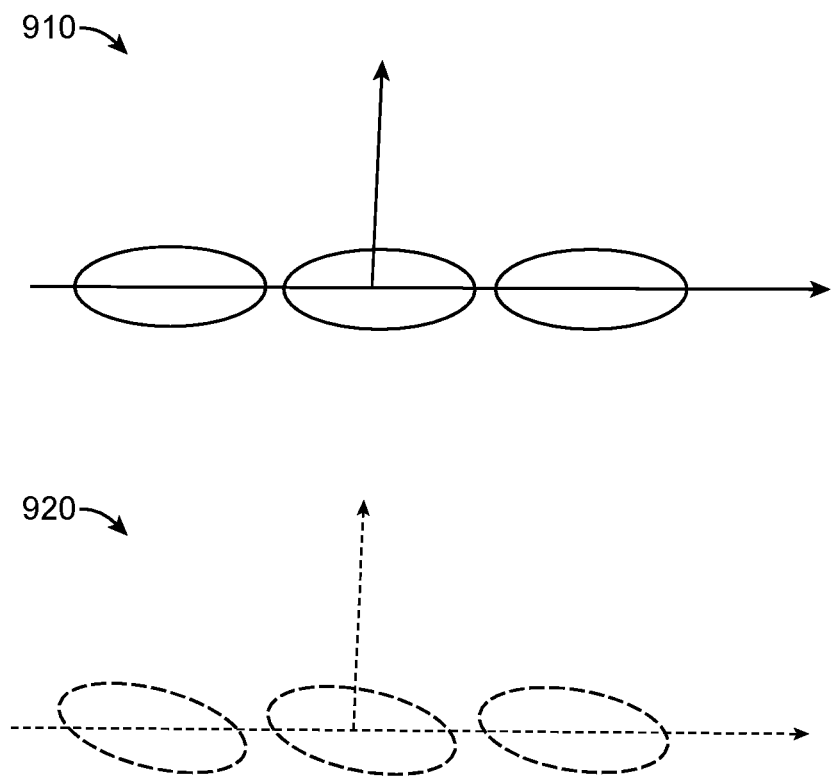
FIG. 9A illustrates an example of a moment model of three teeth with equal rotation, in accordance with one or more embodiments herein.

FIG. 9A illustrates an example of a moment model of three teeth with equal rotation. The relaxed model 910 is shown, and the deformed model 920 is shown. In the illustrated example, all teeth may be in a line and may rotate in z with angle θ and separation distance y. Similar to the previous example, the linear parts may be zero and the quadratic part survives.

Figure 9B:
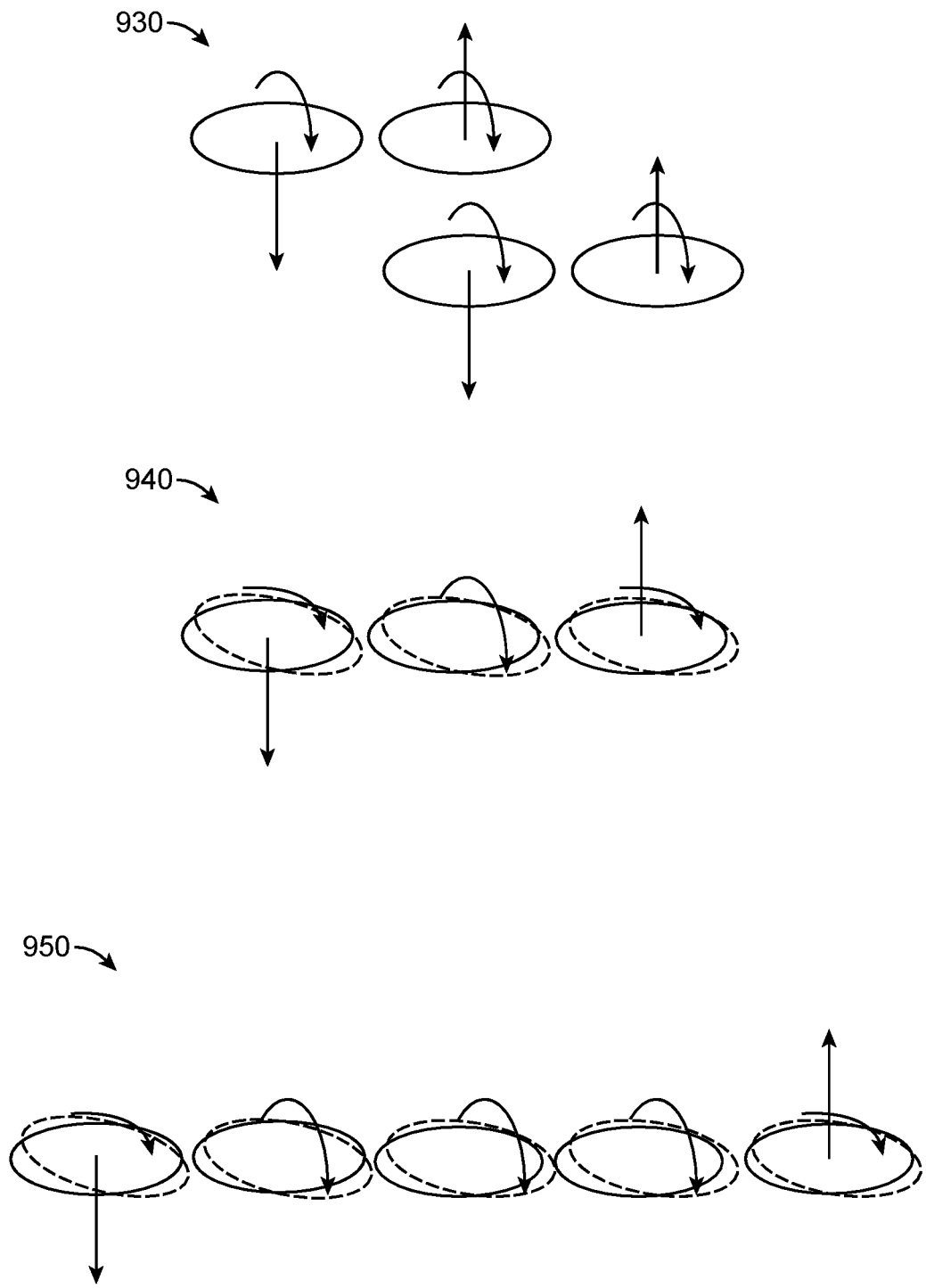
FIG. 9B illustrates the moment model of FIG. 9A where the teeth may be broken into two pairs with a force and moment on each tooth, in accordance with one or more embodiments herein.

As shown in FIG. 9B, the teeth may be broken into two pairs 930 with a force and moment on each tooth. In the example and using the result from the previous example, the force on tooth left from right (F1) may be defined as:

$$F_{12x}=F_{23x}=-\gamma 2\theta y,$$

and the force on tooth right from left (F2) may be defined as:

$$F_{21x}=F_{32x}=\gamma 2\theta y.$$

In the example and using the result from above, the moment on tooth left from right (M1) may be defined as:

$$M_{12z}=M_{23z}=\gamma \theta y^2,$$

and the moment on the tooth right from left (M2) may be defined as:

$$M_{21z}=M_{32z}=\gamma \theta y^2.$$

A force diagram 940 comprising the sum of the forces on each pair is shown. In the example, the total force may be $$F_{1x}=-F_{3x}=-\gamma 2\theta y$$

and $F_2=0$. Similarly, the total moment may be $$M_{1z}=M_{3z}=\gamma \theta y^2,$$

and $M_{2z}=2\gamma \theta y^2$. As shown, the middle tooth may only experience rotation and no force. The example with 4 or more teeth may be derived similarly, and a force diagram is shown 950. Rotation in x may be derived similarly.

Middle Tooth Vertical Translation

Figure 10A:
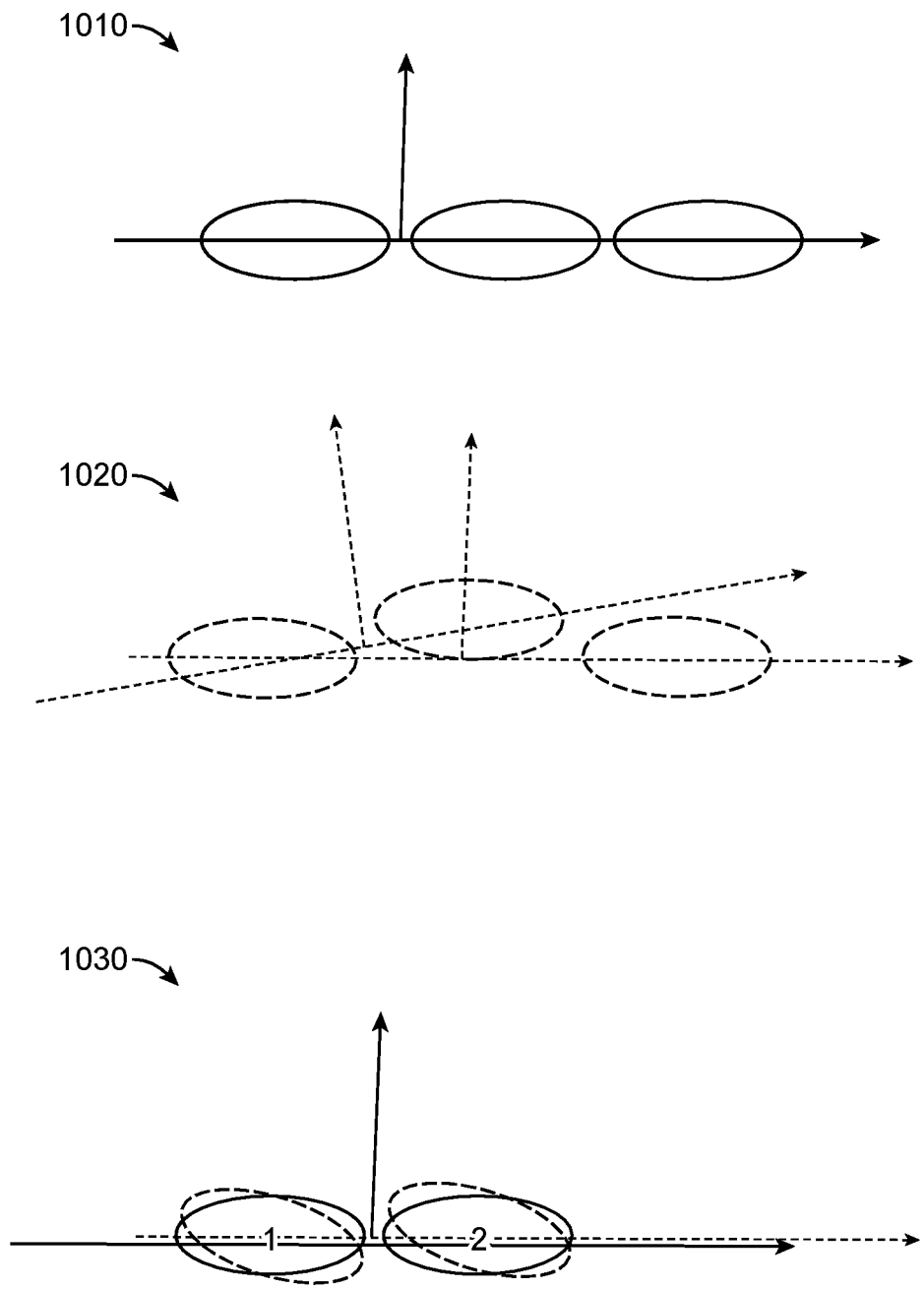
FIG. 10A illustrates an example of a moment model of three teeth with vertical displacement of the middle tooth, in accordance with one or more embodiments herein.

FIG. 10A illustrates an example of a moment model of three teeth with vertical displacement of the middle tooth. The relaxed model 1010 is shown, and the deformed model 1020 is shown. In the illustrated example, the translation in the x direction Tx=t, and the distance between the two teeth is y. Y translation can be represented as $$\delta=\sqrt{y^2+t^2}-y\sim t^2/2,$$

and Z rotation can be represented as $$\theta = \arctan\frac{t}{y}.$$

A map of the relaxed to the deformed model for the left pair 1030 is shown.

Figure 10B:
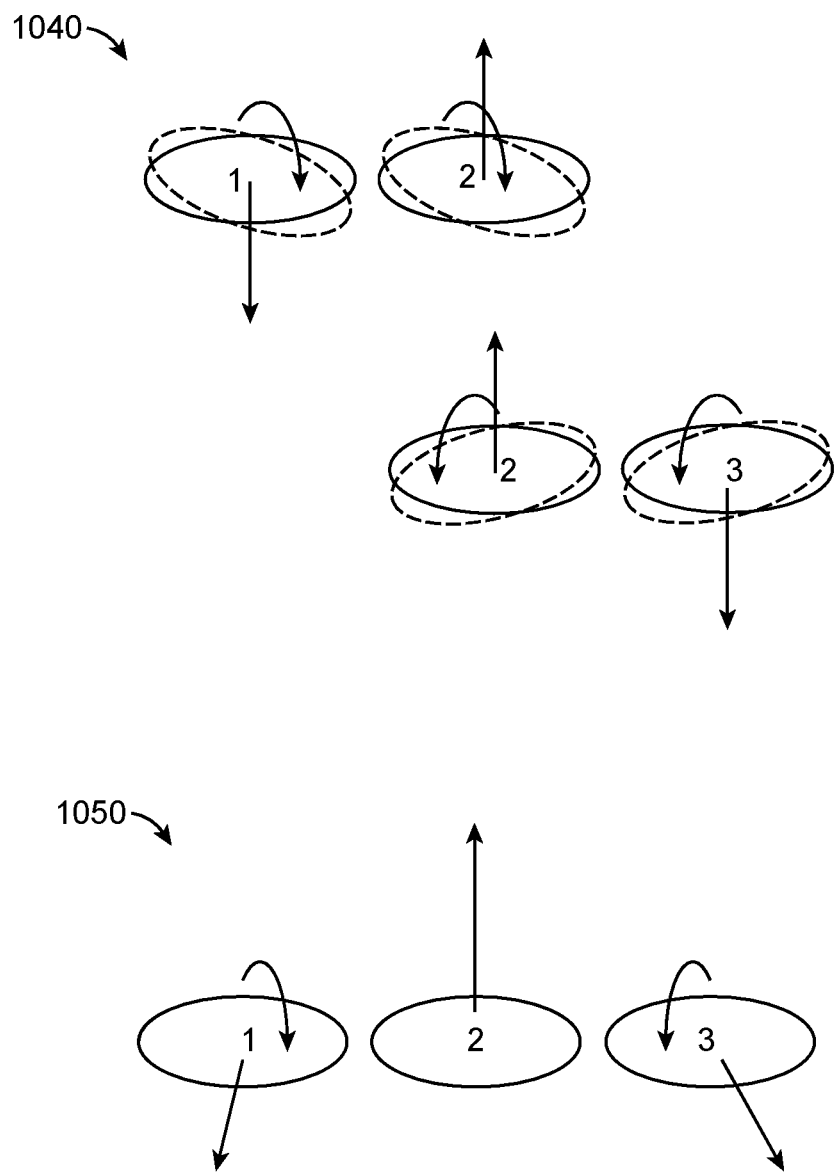
FIG. 10B illustrates the moment model of FIG. 10A where the teeth may be broken into two pairs with a force and moment on each tooth, in accordance with one or more embodiments herein.

As shown in FIG. 10B, the teeth may be broken into two pairs 1040 with a force and moment on each tooth. In the example, the force from y translation may be:

$$F_{21y}=-F_{12y}=\alpha\delta,$$

and from z rotation:

$$F_{21x}=-F_{12x}=\gamma 2\theta y.$$

Similarly, the moment may be $$M_{12z}=M_{21z}=\gamma \theta y^2.$$

Similarly for T2 to T3, Z rotation may be $$-\theta = -\arctan\frac{t}{d}.$$

Therefore, $F_{32y}=-F_{23y}=\alpha\delta$, $-F_{32x}=F_{23x}=\gamma 2\theta y$, and $M_{32z}=M_{23z}=-\gamma \theta y^2$.

A force diagram 1050 comprising the sum of the forces on each pair is shown. The total force on tooth 2 may be expressed as:

$$F_2=F_{23x}+F_{21z}=4\gamma \theta y\hat{x},$$

and the moment $M_{2z}=0$. The total force on tooth 1 may be expressed as:

$$F_1=-\alpha\delta\hat{y}-\gamma 2\theta y\hat{x},$$

and the moment as:

$$M_{1z}=\gamma \theta d^2=-M_{3z}.$$

The force on tooth 3 may be expressed as:

$$F_3 = \alpha\delta\hat{y} - \gamma 2\theta y\hat{x}.$$

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer-implemented method of generating an orthodontic model of tooth movements, the computer-implemented method comprising:
    generating an initial model of a patient dentition, the initial three-dimensional model comprising a first, three-dimensional representation of the patient dentition at a stage of a treatment plan;
    generating a target model of the patient dentition, the target three-dimensional model comprising a second, three-dimensional representation of the patient dentition after the stage of the treatment plan;
    defining a plurality of caps and a plurality of links, wherein each cap of the plurality of caps represents a set of contact points on a tooth of the dentition, and wherein each link of the plurality of links represents a connection between two of the plurality of caps, and wherein each of the plurality of caps comprises a reduced dimensional surface which represents the patient dentition;
    generating a relaxed model of a dental appliance using the plurality of caps and the plurality of links, the relaxed model of the dental appliance representing physical properties of the dental appliance at a first state;
    generating a deformed model of a dental appliance using the plurality of caps and plurality of links, the deformed model of the dental appliance representing the physical properties of the dental appliance at a second state corresponding to a use of the dental appliance;
    determining a plurality of transformational parameters, wherein the plurality of transformational parameters transform the relaxed model to the deformed model and wherein the plurality of transformational parameters are configured to direct the patient dentition from the initial model to the target model; and
    using the plurality of transformation parameters to design the dental appliance.

2. The computer-implemented method of claim 1, wherein the plurality of transformation parameters comprise one or more of a plurality of forces and a plurality of moments.

3. The computer-implemented method of claim 1, further comprising mapping the relaxed model onto the deformed model.

4. The computer-implemented method of claim 1, further comprising expressing the relaxed model and the deformed model in an elastic coordinate system.

5. The computer-implemented method of claim 1, further comprising determining a force system for each pair of teeth.

6. The computer-implemented method of claim 5, further comprising summing the force system for each pair of teeth to determine a total force for a whole arch system.

7. The computer-implemented method of claim 2, further comprising determining a moment system for each pair of teeth.

8. The computer-implemented method of claim 7, further comprising summing the moment system for each pair to determine a total moment for a whole arch system.

9. The computer-implemented method of claim 1, wherein a whole arch system has no total force or total moment.

10. The computer-implemented method of claim 1, wherein the initial model of patient dentition comprises a scan of the patient dentition or a mold of the patient dentition.

11. The computer-implemented method of claim 1, wherein each of the plurality of links comprises a Hookian stiffness parameter.

12. The computer-implemented method of claim 2, further comprising repeating the determining a plurality of moments for a second stage in the treatment plan.

13. The computer-implemented method of claim 1, further comprising fabricating one or a plurality of dental appliances.

14. The computer-implemented method of claim 1, wherein the method reduces a time to generate a force model by 10% relative to solid model analysis.

15. The computer-implemented method of claim 2, further comprising creating or developing the treatment plan based on the plurality of moments.

16. The computer-implemented method of claim 2, further comprising determining an effectiveness of the treatment plan based on the plurality of moments.

17. The computer-implemented method of claim 2, further comprising creating a plurality of treatment plans based on the plurality of moments and selecting a target treatment plan from the plurality of treatment plans.

18. The computer-implemented method of claim 17, wherein selecting the target treatment plan is based on a time efficiency of the target treatment plan.

19. The computer-implemented method of claim 17, wherein selecting the target treatment plan is based on a therapeutic effectiveness of the target treatment plan.

20. The computer-implemented method of claim 2, wherein determining the plurality of tooth moments is performed "chair side".

21. A computer-implemented method of generating an orthodontic treatment plan, the computer-implemented method comprising:
    generating an initial model of a patient dentition, the initial three-dimensional model comprising a first, three-dimensional representation of the patient dentition at a stage of a treatment plan;
    generating a target model of the patient dentition, the target three-dimensional model comprising a second, three-dimensional representation of the patient dentition after the stage of the treatment plan;
    defining a plurality of caps and a plurality of links, wherein each cap of the plurality of caps represents a set of contact points on a tooth of the dentition, and wherein each link of the plurality of links represents a connection between two of the plurality of caps, and wherein each of the plurality of caps comprises a reduced dimensional surface which represents the patient dentition;
    generating a relaxed model of a dental appliance using the plurality of caps and the plurality of links, the relaxed model of the dental appliance representing physical properties of the dental appliance at a first state;

generating a deformed model of a dental appliance using the plurality of caps and plurality of links, the deformed model of the dental appliance representing the physical properties of the dental appliance at a second state corresponding to a use of the dental appliance;

determining a plurality of transformational parameters, wherein the plurality of transformational parameters transform the relaxed model to the deformed model and wherein the plurality of transformational parameters are configured to direct the patient dentition from the initial model to the target model;

using the plurality of transformation parameters to design the dental appliance; and providing the dental appliance to a patient.

22. A system comprising:

memory storing computer-program instructions; and one or more physical processors coupled to the memory, the one or more physical processors configured to implement a computer-implemented method using the computer-program instructions, the computer-implemented method generating a virtual depiction of an orthodontic treatment of a patient, the computer-implemented method comprising:

generating an initial model of a patient dentition, the initial three-dimensional model comprising a first, three-dimensional representation of the patient dentition at a stage of a treatment plan;

generating a target model of the patient dentition, the target three-dimensional model comprising a second, three-dimensional representation of the patient dentition after the stage of the treatment plan;

defining a plurality of caps and a plurality of links, wherein each cap of the plurality of caps represents a set of contact points on a tooth of the dentition, and wherein each link of the plurality of links represents a connection between two of the plurality of caps, and wherein each of the plurality of caps comprises a reduced dimensional surface which represents the patient dentition;

generating a relaxed model of a dental appliance using the plurality of caps and the plurality of links, the relaxed model of the dental appliance representing physical properties of the dental appliance at a first state;

generating a deformed model of a dental appliance using the plurality of caps and plurality of links, the deformed model of the dental appliance representing the physical properties of the dental appliance at a second state corresponding to a use of the dental appliance;

determining a plurality of transformational parameters, wherein the plurality of transformational parameters transform the relaxed model to the deformed model and wherein the plurality of transformational parameters are configured to direct the patient dentition from the initial model to the target model; and using the plurality of transformation parameters to design the dental appliance.

* * * * *